United States Patent
Tanaka et al.

(10) Patent No.: US 10,087,427 B2
(45) Date of Patent: Oct. 2, 2018

(54) GLYCOSYLTRANSFERASE GENE AND USE THEREOF

(71) Applicant: SUNTORY HOLDINGS LIMITED, Osaka-shi, Osaka (JP)

(72) Inventors: Yoshikazu Tanaka, Osaka (JP); Naoko Okitsu, Osaka (JP); Keisuke Matsui, Osaka (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 0 days.

(21) Appl. No.: 15/308,117

(22) PCT Filed: May 1, 2015

(86) PCT No.: PCT/JP2015/063140
§ 371 (c)(1),
(2) Date: Nov. 1, 2016

(87) PCT Pub. No.: WO2015/167016
PCT Pub. Date: May 11, 2015

(65) Prior Publication Data
US 2017/0058269 A1  Mar. 2, 2017

(30) Foreign Application Priority Data
May 2, 2014  (JP) ................................. 2014-095243

(51) Int. Cl.
| C12N 9/12 | (2006.01) |
| C12N 9/10 | (2006.01) |
| A01H 5/00 | (2018.01) |
| C12P 19/60 | (2006.01) |
| C12P 21/00 | (2006.01) |
| C12N 5/10 | (2006.01) |
| C12N 15/09 | (2006.01) |
| C12P 17/06 | (2006.01) |

(52) U.S. Cl.
CPC .............. *C12N 9/1048* (2013.01); *A01H 5/00* (2013.01); *C12N 5/10* (2013.01); *C12N 9/10* (2013.01); *C12N 15/09* (2013.01); *C12P 17/06* (2013.01); *C12P 19/60* (2013.01); *C12P 21/00* (2013.01); *C12Y 204/00* (2013.01)

(58) Field of Classification Search
CPC ................................ C12N 9/1051; C12P 19/18
USPC ......................................................... 435/193
See application file for complete search history.

(56) References Cited

U.S. PATENT DOCUMENTS

2015/0203862 A1*  7/2015  Tanaka .................... A23L 33/10
800/298

FOREIGN PATENT DOCUMENTS

| EP | 2664671 A1 | 11/2013 |
| WO | WO-2012/096307 A1 | 7/2012 |
| WO | WO-2013/108794 A1 | 7/2013 |

OTHER PUBLICATIONS

Eiichiro Ono, et al., "Co-pigmentation and flavonoid glycosyltransferases in blue *Veronica persica* flowers", Phytochemistry, 71 (2010) 726-735.
Judith Isayenkova et al, "Cloning and functional characterisation of two regioselective flavonoid glucosyltransferases from *Beta Vulgaris*," Phytochemistry, 2006, pp. 1598-1612, vol. 67, No. 15.
Masao Hirotani et al., "Cloning and expression of UDP-glucose: flavonoid 7-O-glucosyltransferase from hairy root cultures of *Scutellaria baicalensis*," Planta, 2000, pp. 1006-1013, vol. 210, No. 6.
Jae Hyung Ko et al., "Four glucosyltransferases from rice: cDNA cloning, expression, and characterization," Journal of Plant Physiology, 2008, pp. 435-444, vol. 165, No. 4.
Jeong Ho Kim et al., "Characterization of Flavonoid 7-O-Glucosyltransferase from *Arabidopsis thaliana*," Bioscience, Biotechnology, Biochemistry, 2006, pp. 1471-1477, vol. 70, No. 6.
Akio Noguchi et al, "Local Differentiation of Sugar Donor Specificity of Flavonoid Glycosyltransferase in Lamiales," The Plant Cell, May 2009, pp. 1556-1572, vol. 21, No. 5.
International Search Report dated Jul. 7, 2015 in PCT/JP2015/063140 filed May 1, 2015.

* cited by examiner

*Primary Examiner* — Tekchand Saidha
(74) *Attorney, Agent, or Firm* — Drinker Biddle & Reath LLP

(57) ABSTRACT

Provided is a polynucleotide encoding a protein that exhibits activity for transferring a sugar to a hydroxyl group at position 7 of a flavone, particularly flavone 4'-glucoside, wherein the polynucleotide is selected from the group consisting of: (a) a polynucleotides comprising the base sequence of SEQ ID NO: 1 or SEQ ID NO: 5; (b) a polynucleotide that hybridizes, under stringent conditions, with a polynucleotide comprising the base sequence complementary to the base sequence of SEQ ID NO: 1 or SEQ ID NO: 5; (c) a polynucleotide encoding a protein comprising the amino acid sequence of SEQ ID NO: 2 or SEQ ID NO: 6; (d) a polynucleotide encoding a protein comprising an amino acid sequence in which one or more amino acids have been deleted, substituted, inserted, and/or added in the amino acid sequence of SEQ ID NO: 2 or SEQ ID NO: 6.

22 Claims, 11 Drawing Sheets
Specification includes a Sequence Listing.

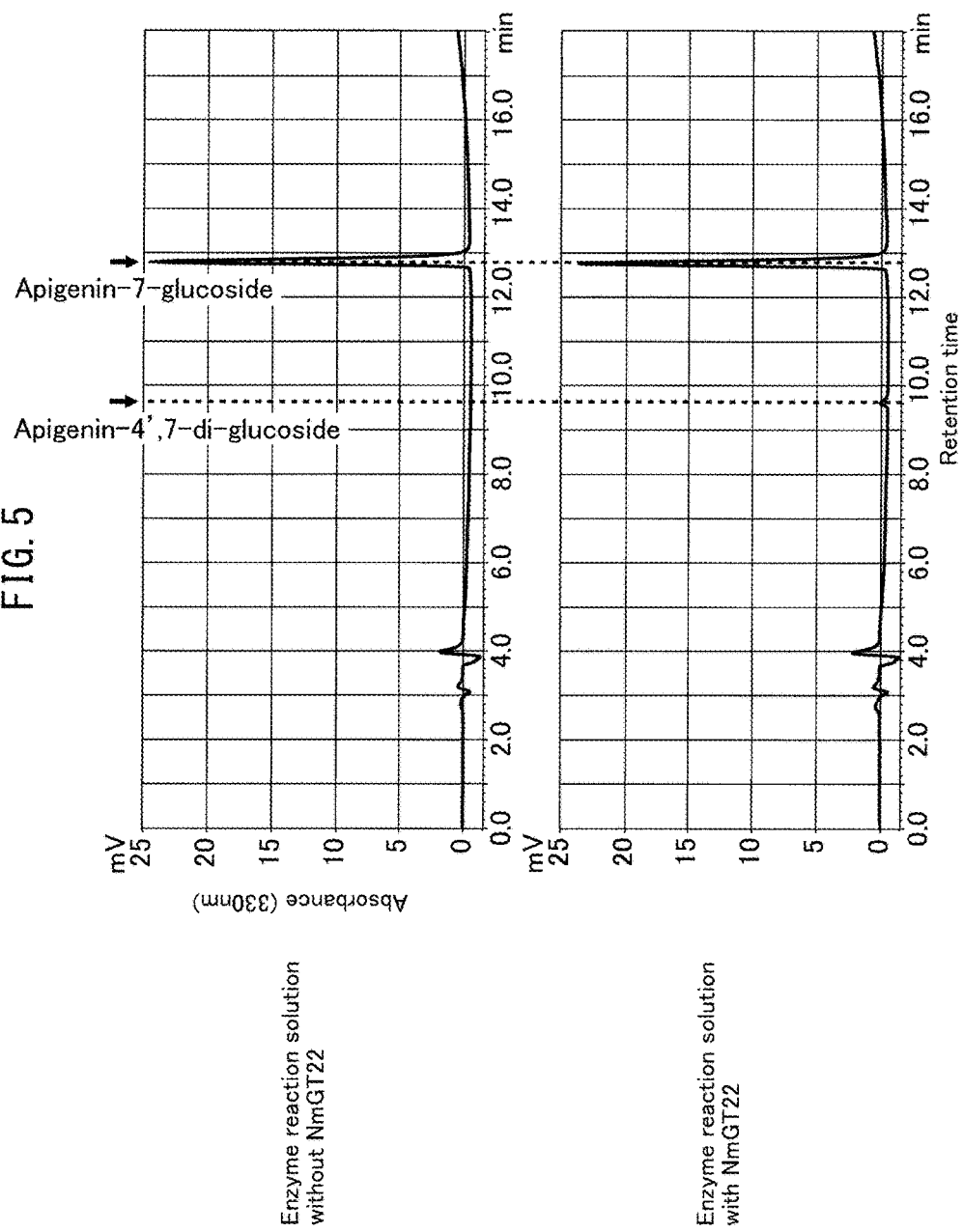

FIG. 6

Results of Experiment for Measuring Enzyme Activity in Vitro

| Substrate | Reaction rate (%) | Reaction product |
|---|---|---|
| Apigenin | 77.16 | Apigenin-7-glucoside |
| Apigenin-4'-glucoside | 100 | Apigenin-4',7-di-glucoside |
| Apigenin-7-glucoside | 2.69 | |
| Luteolin | 99.07 | Luteolin-7-glucoside |
| Luteolin-4'-glucoside | 99.68 | Luteolin-4',7-di-glucoside |
| Luteolin-7-glucoside | 16.10 | |
| Tricetin | 97.91 | |
| Kaempferol | 73.99 | |
| Kaempferol-3-glucoside | 1.16 | |
| Quercetin | 86.32 | |
| Quercetin-3-glucoside | 5.90 | |
| Myricetin | 100 | |
| Pelargonidin | 88.35 | |
| Pelargonidin-3-glucoside | 96.37 | Pelargonidin-3,5-di-glucoside |
| Cyanidin | 73.90 | |
| Cyanidin-3-glucoside | 97.54 | Cyanidin-3,5-di-glucoside |
| Delphinidin | 71.34 | |
| Delphinidin-3-glucoside | 95.98 | Delphinidin-3,5-di-glucoside |
| Petunidin | 78.37 | |
| Isovitexin | 0.00 | |
| betanidin | 0.00 | | flavone: Apigenin through Tricetin
flavonol: Kaempferol through Myricetin
anthocyanin: Pelargonidin through Petunidin

FIG. 7

Sequence alignment of NmGT22 and Vitis_vinifera_cultivar_Maccabeu_GT2.

FIG. 11

```
NmGT22      1 MECKNPDSLHVFLVSAPGQGNVTPMLRLAKSLASKGLLVTFSTPESYGKEMRKTND PISDQPILIGEGS IRPEFLDDEWDENEHKGEGLDAYATHLERVG 100
NmGT22-H    1 MECKNPDSLHVFLVSAPGQGNVTPMLRLAKSLASKGLLVTFSTPESYGKEMRKTN  PISDQPILIGEG  IRPEFLDDEWDENEHKGEGLDAYATHLERVG 100

NmGT22    101 KQ L PRMFKKHEEEGRPISCIINNPFIPWVPEVAESLGIPSALLWVQSCASFSSYYHFFNDLVSFPTESNLKKDVCLPSMPMLKYDEVPLLLYPIVPLP  200
NmGT22-H  101 KQ IL PRMFKKHEEEGRPISCIINNPFIPWVPEVAESLGIPSALLWVQSCASFSSYYHFFNDLVSFPTESNLKKDVCLPSMPMLKYDEVPLLLYPIVPLP  200

NmGT22    201 ISLKNAMLRQQKNLSKTFCVLVDTFQQLEDELIHYLSKLCPIRPIGPLFKISDTSSSNISGDIRKADDCIEWLDSKSPSSVVYISFGSIVHLKQEQITEI 300
NmGT22-H  201 ISLKNAMLRQQKNLSKTFCVLVDTFQQLEDELIHYLSKLCPIRPIGPLFKISDTSSSNISGDIRKADDCIEWLDSKSPSSVVYISFGSIVHLKQEQITEI 300

NmGT22    301 AYALMNINISFLWVMEPPQKDSYDKQHVLPQGFLEKVGEEKGKVVKWSPQEQVLSHQSLACFVTHCGWNSSMEALANGIRVVTLPQWGDQVINAKPLVDVF 400
NmGT22-H  301 AYALMNINISFLWVMKPPQEDSYDKQHVLPQGFLEKVGEKGKVVKWSPQEQVLSHQSLACFVTHCGWNSSMEALANGIRVVTLPQWGDQVINAKPLVDVF 400

NmGT22    401 GVGVRLSRGDLEDRIIPREEIELRLLEVTSGEKATEMKHNALRWKKAAEEAVAKDGSSKNLQEFVDELNNFRFIT 476
NmGT22-H  401 GVGVRLSRGDLEDRIIPREEIELRLLEVTSGEKATEMKHNALRWKKAAEEAVAKDGSSKNLQEFVDELNNFRFIT 476
```

GLYCOSYLTRANSFERASE GENE AND USE THEREOF

CROSS REFERENCE TO RELATED APPLICATIONS

This application is the National Stage of International Application No. PCT/JP2015/063140 filed May 1, 2015 and claims benefit of Japanese Application No. 2014-095243 filed on May 2, 2014.

SEQUENCE LISTING

The instant application contains a sequence listing which has been submitted in ASCII format via EFS-Web and is hereby incorporated by reference in its entirety. Said ASCII copy, created on Apr. 1, 2018, is named substitute_047237_5038_548593_ST25.txt and is 23,944 bytes in size.

TECHNICAL FIELD

The present invention relates to a polynucleotide encoding a protein having activity that transfers a sugar to the hydroxyl group of a flavone, and particularly flavone 4'-glycoside, and to the use thereof.

BACKGROUND ART

Flowers having new traits are always considered to have high value in the flower industry. The development of plants capable of inducing a change in color, considered to be the most important trait among flowers, is viewed with particular importance, and various colors of flowers have been developed thus far through selective breeding using classic crossbreeding techniques. Although crossbreeding is an effective method of selective breeding, since plants are subjected to their own unique genetic limitations, they have the shortcoming of only allowing the use of the genetic resources of related species able to be crossbred therewith. For example, despite having been crossbred for many years, violet to blue roses, carnations, chrysanthemums and lilies, bright red gentians and irises, and yellow morning glories have yet to be produced.

Flower color is attributable to four types of pigments consisting of flavonoids, carotenoids, chlorophylls and betalains. Among these, flavonoids exhibit a diverse range of colors in the manner of yellow, red and blue. The group of flavonoids exhibiting red, violet and blue colors are generically referred to as anthocyanins, and the structural diversity of anthocyanins is one of the reasons for the diverse range of flower color. When considering the biosynthetic pathway thereof, anthocyanins can be broadly classified into three groups according to their aglycone structure. Pelargonidin-type anthocyanins are frequently contained in flowers having bright red color in the manner of carnations and geraniums, while delphinidin-type anthocyanins are frequently contained in flowers having blue or violet color. The reason for the absence of blue or violet varieties among roses, carnations, chrysanthemums and lilies is that these plants do not have the ability to synthesize delphinidin-type anthocyanins.

In addition to the accumulation of delphinidin, any of the following other factors are considered to be required to allow flowers to have blue color: (i) the anthocyanin must be modified by one or a plurality of aromatic acyl groups, (ii) the anthocyanin must be present together with a copigment such as flavone or flavonol, (iii) iron ions or aluminum ions must be present together with the anthocyanin, (iv) the pH of vacuoles in which the anthocyanin is localized must rise from a neutral pH to a weakly alkaline pH, or (5) the anthocyanin, copigment and metal ions must form a complex (and such anthocyanins are referred to as metalloanthocyanins) (refer to Non-Patent Document 1).

Considerable research has been conducted on flavonoid and anthocyanin biosynthesis, and related biosynthetic enzymes and genes encoding those enzymes have been identified (refer to Non-Patent Document 2). For example, the gene for flavonoid-3',5'-hydroxylase (F3'5'H), which hydroxylates the flavonoid B ring required for biosynthesis of delphinidin, is obtained from numerous plants. In addition, by introducing these F3'5'H gens into carnations (refer to Patent Document 1), roses (refer to Non-Patent Document 3 and Patent Documents 2 and 3) or chrysanthemums (refer to Patent Document 4), a genetically modified plant is produced in which delphinidin accumulates in the flower petals thereof and flower color changes to blue (refer to Non-Patent Document 4). Such carnations and roses are available commercially.

Flavones are a type of organic compound in the form of cyclic ketones derived from flavans, and in the narrow sense, refer to 2,3-dehydroflavan-4-one, a compound represented by the chemical formula $C_{15}H_{10}O_2$ and having a molecular weight of 222.24. In the broad sense, derivatives belonging to flavones are generically referred to as "flavones". Flavones in the broad sense (flavones) constitute one category of flavonoids, and those flavonoids having a flavone structure for the basis skeleton thereof and not having a hydroxyl group at position 3 are classified as "flavones". Typical examples of "flavones" include apigenin (4',5,7-trihydroxyflavone) and luteolin (3',4',5,7-tetrahydroxyflavone). In the description of the present application, the term "flavones" refers to flavones in the broad sense, namely derivatives belonging to flavones.

Genes for flavone synthases (FNS) required for biosynthesis of flavones are obtained from numerous plants. Flavones are known to have the effect of producing the deep blue color of anthocyanins when in the presence of anthocyanins, and these FNS genes are attracting attention in the field of flower color modification. As a result of introducing an FNS gene into a rose not having the ability to synthesize flavones together with F3'5'H, simultaneous to accumulation of delphinidin in flower petals, flavones also accumulate therein causing flower color to change to an even bluer color (refer to Patent Document 5). In addition to producing a blue flower color, since flavones also absorb ultraviolet rays, they have the function of protecting plants from ultraviolet rays or serving as a visual signal for insects in the case of insect-pollinated flowers. In addition, flavones are also involved in interaction between plants and soil microorganisms. Moreover, flavones are also used as ingredients of foods and cosmetics as components that are beneficial for health. For example, flavones are said to have an anticancer action, and the ingestion of foods containing large amounts of flavones has been demonstrated to treat or prevent cancer.

In addition, genes that modify anthocyanins and flavones are obtained from numerous plants. Although examples thereof include glucosyltransferases, acyltransferases and methyltransferases, glucosyltransferases (GT) that transfer glucose to the hydroxyl group at position 3 of anthocyanins are described here. For example, genes that encode proteins having activity that transfers glucose to the hydroxyl group at position 3 of an anthocyanin have been isolated from such plants as gentians, perillas, petunias, roses or snapdragons (refer to Non-Patent Documents 4 to 6 and Patent Document 6). Genes that encode proteins having activity that transfers glucose to the hydroxyl group at position 5 of an anthocyanin have been isolated from such plants as perillas, petunias, gentians, verbenas or torenias (refer to Non-Patent Documents 5 to 7 and Patent Document 7). Genes that encode proteins having activity that transfers glucose to the hydroxyl group at position 7 of a flavone have been isolated from thale cress (refer to Non-Patent Document 8). A gene that encodes a protein having activity that transfers glucose to the hydroxyl group at position 7 of baicalin has been isolated from baical skullcap, and a protein obtained by expressing this gene in *Escherichia coli* (*E. coli*) has been reported to catalyze a reaction that demonstrates activity that transfers glucose to the hydroxyl group at position 7 of a flavonoid (refer to Non-Patent Document 9). Genes that encode a protein having activity that transfers glucose to the hydroxyl group at position 3' of an anthocyanin have been isolated from gentians, butterfly peas and florist's *cineraria* (refer to Patent Document 8). In addition, a gene that encodes a protein having activity that sequentially transfers glucose to hydroxyl groups at two different locations on the A ring and C ring of an anthocyanin has been isolated from roses (refer to Patent Document 9). A gene that encodes a protein having activity that sequentially transfers glucose to two different locations on the B ring of an anthocyanin has been isolated from butterfly peas (refer to Patent Document 10).

Although the aforementioned glucosyltransferases use UDP-glucose as a glycosyl donor, glucosyltransferases have recently been identified that use acyl-glucose as a glycosyl donor. A gene that encodes a protein having activity that transfers glucose to the hydroxyl group at position 5 of anthocyanidin 3-glucoside has been isolated from carnations, while a gene that encodes a protein having activity that transfers glucose to the hydroxyl at position 7 has been isolated from larkspur (refer to Non-Patent Documents 10 and 13). Moreover, a protein obtained by expressing a glucosyltransferase gene derived from Livingstone daisies has been reported to demonstrate activity that transfers glucose to either of the hydroxyl groups at position 4' or position 7' of a flavonoid in vitro (refer to Non-Patent Document 11). In addition, a polynucleotide that encodes a protein having activity that transfers a sugar to the hydroxyl group at position 4' of a flavone has been isolated from Nemophilas (refer to Patent Document 11).

In this manner, although there are numerous glucosyltransferases in the form of proteins having activity that transfer glucose to various hydroxyl groups, there are still thought to be a large number of glucosyltransferases for which the function thereof has yet to be identified. Thus, there continues to be a need to acquire glucosyltransferases that function in plants and are useful for modifying flower color.

PRIOR ART DOCUMENTS

Patent Documents

[Patent Document 1] International Publication No. WO 2006/105598
[Patent Document 2] International Publication No. WO 2010/122849
[Patent Document 3] International Publication No. WO 2005/017147
[Patent Document 4] International Publication No. WO 2009/062253
[Patent Document 5] International Publication No. WO 2008/156211
[Patent Document 6] International Publication No. WO 2007/094521
[Patent Document 7] International Publication No. WO 99/05287
[Patent Document 8] International Publication No. WO 01/092509
[Patent Document 9] Japanese Unexamined Patent Publication No. 2006-149293
[Patent Document 10] Japanese Unexamined Patent Publication No. 2005-95005
[Patent Document 11] International Publication No. WO 2013/108794
[Patent Document 12] International Publication No. WO 2012/096307

Non-Patent Documents

[Non-Patent Document 1] Natural Product Reports (2009), 26, 884-915
[Non-Patent Document 2] Biosci. Biotechnol. Biochem. (2010), 74(9), 1760-1769
[Non-Patent Document 3] Plant Cell Physiol. (2007), 48(11), 1589-1600
[Non-Patent Document 4] Plant Cell Physiol. (1996), 37(5), 711-716
[Non-Patent Document 5] J. Biol. Chem. (1999), 274(11), 7405-7411
[Non-Patent Document 6] Plant Molecular Biology (2002), 48, 401-411
[Non-Patent Document 7] Journal of Experimental Botany (2008), 59(6), 1241-1252
[Non-Patent Document 8] Biosci. Biotechnol. Biochem. (2006), 70(6), 1471-1477
[Non-Patent Document 9] Planta (2000), 210, 1006-1013
[Non-Patent Document 10] Plant Cell (2010), 22(10), 3374-3389
[Non-Patent Document 11] The Plant Journal (1999), 19(5), 509-519
[Non-Patent Document 12] Threes (2007), 21, 521-529
[Non-Patent Document 13] Plant Cell (2003), 25(10), 4150-4165

DISCLOSURE OF THE INVENTION

Problems to be Solved by the Invention

Alteration of the physical properties of flavones is required in order to change flower color as well as develop the components of foods, pharmaceuticals and cosmetics. For example, although the color of carnations, roses and chrysanthemums in which delphinidin has accumulated is bluish-violet, research is being conducted to make this color even bluer.

Metalloanthocyanins represented by the pigments of Centaureas, Commelinas, Salvias and Nemophilas are composed of 6 anthocyanin molecules, 6 flavone molecules and 2 metal ions, and each component congregates to form a stable blue pigment. For example, the metalloanthocyanin of *Nemophila* is formed from nemophilin, malonyl apigenin 4',7'-diglucoside, $Mg^{2+}$ and $Fe^{3+}$. The metalloanthocyanin of *Salvia* is formed from cyanosalvianin, apigenin 4',7'-diglucoside and Me. According to previous research, all blue flowers that form metalloanthocyanins biosynthesize flavones in which a sugar is added to both hydroxyl groups at position 4' and position 7, and the sugars added to these flavones have been determined to play an important role in molecular recognition during metalloanthocyanin formation. Molecular recognition is important during the formation of sugars coordinated at position 4' of flavones, and the sugar at position 7 has been shown to contribute to the stability thereof (Non-Patent Document 1). Metalloanthocyanins are first formed when these two sugars are added to a flavone, resulting in the expression of beautiful blue color.

With the foregoing in view, an object to be achieved by the present invention is to provide a polynucleotide, which encodes a protein having activity that specifically transfers a sugar to the hydroxyl group at position 7 of a flavone, and particularly flavone 4'-glucoside, and a use thereof.

Means for Solving the Problems

As a result of conducting extensive studies and experiments to solve the aforementioned problems, the inventor of the present application isolated a polynucleotide that encodes a protein having activity that transfers a sugar to the hydroxyl group at position 7 of a flavone, and particularly flavone 4'-glucoside, and confirmed that this polynucleotide can be used, thereby leading to completion of the present invention.

Namely, the present invention is as indicated below.

[1] A polynucleotide selected from the group consisting of the following (a) to (e):

(a) a polynucleotide composed of the base sequence of SEQ ID NO: 1 or SEQ ID NO: 5;

(b) a polynucleotide that hybridizes under stringent conditions with a polynucleotide composed of a base sequence complementary to the base sequence of SEQ ID NO: 1 or SEQ ID NO: 5, and encodes a protein having activity that transfers a sugar to the hydroxyl group at position 7 of a flavone;

(c) a polynucleotide that encodes a protein composed of the amino acid sequence of SEQ ID NO: 2 or SEQ ID NO: 6;

(d) a polynucleotide that encodes a protein composed of an amino acid sequence in which one or a plurality of amino acids have been deleted, substituted, inserted and/or added in the amino acid sequence of SEQ ID NO: 2 or SEQ ID NO: 6, and has activity that transfers a sugar to the hydroxyl group at position 7 of a flavone; and, (e) a polynucleotide that encodes a protein that has an amino acid sequence having identity of 90% or more with the amino acid sequence of SEQ ID NO: 2 or SEQ ID NO: 6, and has activity that transfers a sugar to the hydroxyl group at position 7 of a flavone.

[2] The polynucleotide described in [1] above, which is a polynucleotide composed of the base sequence of SEQ ID NO: 1 or SEQ ID NO: 5.

[3] The polynucleotide described in [1] above, which is a polynucleotide that encodes a protein composed of the amino acid sequence of SEQ ID NO: 2 or SEQ ID NO: 6.

[4] The polynucleotide described in [1] above, which is a polynucleotide that hybridizes under stringent conditions with a polynucleotide composed of a base sequence complementary to the base sequence of SEQ ID NO: 1 or SEQ ID NO: 5, and encodes a protein having activity that transfers a sugar to the hydroxyl group at position 7 of flavone 4'-glucoside.

[5] The polynucleotide described in [1] above, which is a polynucleotide that encodes a protein that has an amino acid sequence having identity of 95% or more with the amino acid sequence of SEQ ID NO: 2 or SEQ ID NO: 6, and has activity that transfers a sugar to the hydroxyl group at position 7 of flavone 4'-glucoside.

[6] A protein encoded by the polynucleotide described in any of [1] to [5] above.

[7] A vector containing the polynucleotide described in any of [1] to [5] above.

[8] The vector described in [7] above, further containing a polynucleotide selected from the group consisting of the following (f) to (j):

(f) a polynucleotide composed of the base sequence of SEQ ID NO: 3;

(g) a polynucleotide that hybridizes under stringent conditions with a polynucleotide composed of a base sequence complementary to the base sequence of SEQ ID NO: 3, and encodes a protein having activity that transfers a sugar to the hydroxyl group at position 4' of a flavone;

(h) a polynucleotide that encodes a protein composed of the amino acid sequence of SEQ ID NO: 4;

(i) a polynucleotide that encodes a protein that is composed of an amino acid sequence in which one or a plurality of amino acids have been deleted, substituted, inserted and/or added in the amino acid sequence of SEQ ID NO: 4, and has activity that transfers a sugar to the hydroxyl group at position 4' of a flavone; and, (e) a polynucleotide that encodes a protein that has an amino acid sequence having identity of 90% or more with the amino acid sequence of SEQ ID NO: 4, and has activity that transfers a sugar to the hydroxyl group at position 4' of a flavone.

[9] A non-human host introduced with the vector described in [7] or [8] above.

[10] A method for adding a sugar to the hydroxyl group at position 7 of a flavone using the polynucleotide described in any of [1] to [5] above.

[11] The method described in [10] above, wherein the flavone is flavone 4'-glucoside.

[12] A plant, progeny thereof, portion thereof or tissue thereof introduced with the polynucleotide described in any of [1] to [5] above.

[13] The plant, progeny thereof, portion thereof or tissue thereof described in [12] above, further introduced with a polynucleotide selected from the group consisting of the following (f) to (i):

(f) a polynucleotide composed of the base sequence of SEQ ID NO: 3;

(g) a polynucleotide that hybridizes under stringent conditions with a polynucleotide composed of a base sequence complementary to the base sequence of SEQ ID NO: 3, and encodes a protein having activity that transfers a sugar to the hydroxyl group at position 4' of a flavone;

(h) a polynucleotide that encodes a protein composed of the amino acid sequence of SEQ ID NO: 4;

(i) a polynucleotide that encodes a protein that is composed of an amino acid sequence in which one or a plurality of amino acids have been deleted, substituted, inserted and/or added in the amino acid sequence of SEQ ID NO: 4, and has activity that transfers a sugar to the hydroxyl group at position 4' of a flavone; and, (e) a polynucleotide that encodes a protein that has an amino acid sequence having identity of 90% or more with the amino acid sequence of SEQ ID NO: 4, and has activity that transfers a sugar to the hydroxyl group at position 4' of a flavone.

[14] The portion of a plant described in [12] or [13] above, which is a cut flower.

[15] A processed cut flower that uses the cut flower described in [14] above.

[16] A method for producing a protein having activity that transfers a sugar to the hydroxyl group at position 7 of a flavone, comprising the following steps:

culturing or growing the non-human host described in [9] above, and harvesting a protein having activity that transfers a sugar to the hydroxyl group at position 7 of a flavone from the non-human host.

[17] The method described in [16] above, wherein the flavone is flavone 4'-glucoside.

[18] A method for producing a flavone in which a sugar has been added to the hydroxyl group at position 7, comprising the following steps:

culturing or growing the non-human host described in [9] above, and harvesting a flavone in which a sugar has been added to the hydroxyl group at position 7 from the non-human host.

[19] The method described in [18] above, wherein a sugar is also added to the hydroxyl group at position 4' of the flavone.

[20] A composition containing a flavone in which a sugar has been added to the hydroxyl groups at positions 4' and 7 produced according to the production method described in [19] above.

Effects of the Invention

A protein having activity that specifically transfers a sugar to the hydroxyl group at position 7 of a flavone, and particularly flavone 4'-glucoside, can be produced by expressing the polynucleotide of the present invention in a suitable host cell. According to the present invention, a protein having activity that transfers a sugar to the hydroxyl group at position 7 of a flavone, and particularly flavone 4-glucoside, can be used to modify flower color by expressing constitutively or tissue-specifically in a plant.

A flavone having a sugar added to both the hydroxyl groups at position 4' and position 7 can be easily formed by introducing a protein having activity that transfers a sugar to the hydroxyl group at position 7 of a flavone, and particularly flavone 4'-glucoside, into a plant. A flavone having a sugar added to the hydroxyl groups at position 4' and position 7 can be preferably formed by expressing a protein having activity that transfers a sugar to hydroxyl group at position 4' of a flavone in a plant together with a protein having activity that transfers a sugar to the hydroxyl group at position 7.

In addition, according to the present invention, a method for producing a flavone having a sugar added to the hydroxyl group at position 7, and particularly a flavone having a sugar added to both hydroxyl groups at position 4' and position 7, and a composition containing a flavone obtained according to that production method, are provided.

BRIEF DESCRIPTION OF THE DRAWINGS

FIG. 5 is a high-performance liquid chromatogram of a liquid in which a solution of NmGT22 protein and apigenin 7-glucoside underwent an enzymatic reaction.

FIG. 6 is a table summarizing the reactivity of NmGT22 protein with various types of flavonoid substrates.

FIG. 7 is a sequence alignment diagram comparing the amino acid sequence of NmGT22 (SEQ ID NO: 2) with those of enzymes that add a sugar to hydroxybenzoic acid or cinnamic acid in grapes (VvgGT22) (SEQ ID NO: 13).

FIG. 11 is a sequence alignment diagram comparing the amino acid sequences of NmGT22 (SEQ ID NO: 2) and NmGT22-II (SEQ ID NO: 6).

BEST MODE FOR CARRYING OUT THE INVENTION

Figure 1:
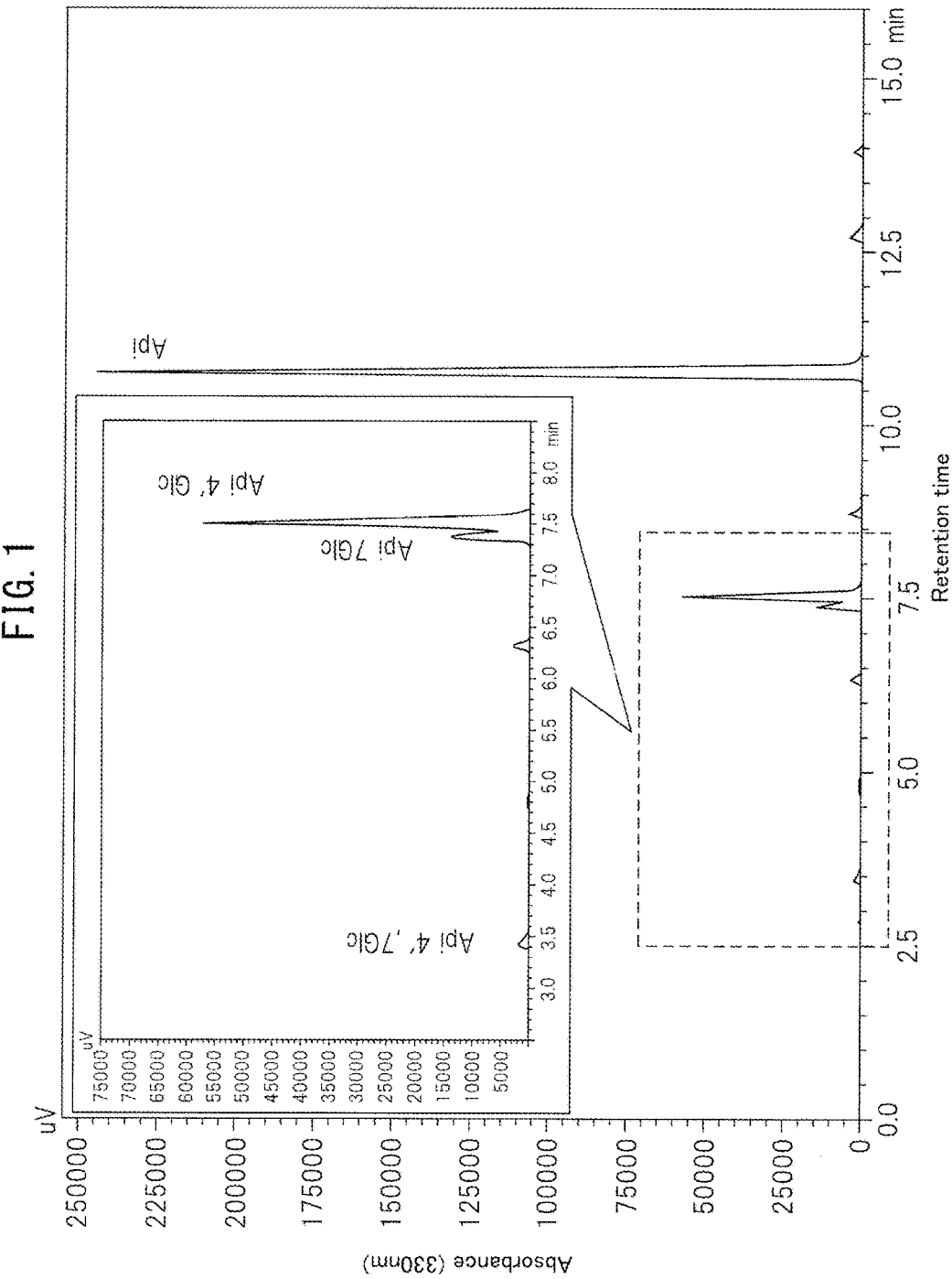
FIG. 1 is a high-performance liquid chromatogram of a liquid in which a flower petal extract and apigenin underwent an enzymatic reaction.

The present invention relates to a polynucleotide selected from the group consisting of:

(a) a polynucleotide composed of the base sequence of SEQ ID NO: 1 or SEQ ID NO: 5;

(b) a polynucleotide that hybridizes under stringent conditions with a polynucleotide composed of a base sequence complementary to the base sequence of SEQ ID NO: 1 or SEQ ID NO: 5, and encodes a protein having activity that transfers a sugar to the hydroxyl group at position 7 of a flavone;

(c) a polynucleotide that encodes a protein composed of the amino acid sequence of SEQ ID NO: 2 or SEQ ID NO: 6;

(d) a polynucleotide that encodes a protein composed of an amino acid sequence in which one or a plurality of amino acids have been deleted, substituted, inserted and/or added in the amino acid sequence of SEQ ID NO: 2 or SEQ ID NO: 6, and has activity that transfers a sugar to the hydroxyl group at position 7 of a flavone; and, (e) a polynucleotide that encodes a protein that has an amino acid sequence having identity of 90% or more with the amino acid sequence of SEQ ID NO: 2 or SEQ ID NO: 6, and has activity that transfers a sugar to the hydroxyl group at position 7 of a flavone.

In the present description, the term "polynucleotide" refers to DNA or RNA.

In the present description, the term "stringent conditions" refers to conditions that allow a polynucleotide or oligonucleotide to selectively, detectably and specifically bind with genomic DNA. Stringent conditions are defined by a suitable combination of salt concentration, organic solvent (such as formamide) concentration, temperature and other known conditions. Namely, stringency is increased by reducing salt concentration, increasing organic solvent concentration or raising hybridization temperature. Moreover, washing conditions following hybridization also have an effect on stringency. These washing conditions are also defined by salt concentration and temperature, and washing stringency increases as a result of reducing salt concentration and raising temperature. Thus, the term "stringent conditions" refers to conditions under which there is specific hybridization only between base sequences having a high degree of identity such that the degree of identity between each base sequence is, for example, about 80% or more on average overall, preferably about 90% or more, more preferably about 95% or more, even more preferably 97% or more, and most preferably 98% or more. Examples of "stringent conditions" include conditions such that sodium concentration is 150 mM to 900 mM and preferably 600 mM to 900 mM at a pH of 6 to 8 and temperature of 60° C. to 68° C. Specific examples include carrying out hybridization under conditions consisting of 5×SSC (750 mM NaCl, 75 mM trisodium citrate), 1% SDS, 5×Denhardt's solution, 50% formaldehyde and 42° C., and carrying out washing under conditions consisting of 0.1×SSC, (15 mM NaCl, 1.5 mM trisodium citrate), 0.1% SDS and 55° C.

Hybridization can be carried out in accordance with, for example, a method known in the art or a method in compliance therewith such as the method described in Current Protocols in Molecular Biology (edited by Frederick M. Ausubel et al.). In addition, in the case of using a commercially available library, hybridization can be carried out in accordance with the method described in the usage manual provided therewith. Genes selected by such hybridization may be naturally-occurring genes, such as plant-derived genes, or non-plant-derived genes. In addition, genes selected by hybridization may be cDNA, genomic DNA or chemically synthesized DNA.

The aforementioned phrase "amino acid sequence in which one or a plurality of amino acids have been deleted, substituted, inserted and/or added" refers to an amino acid sequence in which an arbitrary number of amino acids, such as 1 to 20, preferably 1 to 5 and more preferably 1 to 3, have been deleted, substituted, inserted and/or added. A type of genetic engineering technique in the form of site-specific mutagenesis is useful since it is a technique that enables a specific mutation to be introduced at a specific location, and can be carried out in compliance with the method described in Molecular Cloning: A Laboratory Manual, 2nd Ed., Cold Spring Harbor Laboratory Press, Cold Spring Harbor, N.Y., 1989. A protein composed of an amino acid sequence in which one or a plurality of amino acids have been deleted, substituted, inserted and/or added can be obtained by expressing this mutated DNA using a suitable expression system.

In addition, the DNA according to the present invention can be obtained by a method known among persons with ordinary skill in the art, such as methods in which DNA is synthesized chemically such as the phosphoamidide method, or nucleic acid amplification methods that use a nucleic acid sample of a plant as a template and use primers designed based on the nucleotide sequence of a target gene.

In the present description, the term "identity" refers to the amount (number) of amino acid residues or base residues composing the chains of two polypeptide sequences (or amino acid sequences) or polynucleotide sequences (or base sequences) for which their mutual matching relationship can be determined to be identical, refers to the degree of sequence correlation between two polypeptide sequences or two polynucleotide sequences, and can be calculated easily. Numerous methods are known for measuring identity between two polynucleotide sequences or two polypeptide sequences, and the term "identity" is known among persons with ordinary skill in the art (see, for example, Lesk, A. M. (Ed.), Computational Molecular Biology, Oxford University Press, New York (1988); Smith, D. W. (Ed.), Biocomputing: Informatics and Genome Projects, Academic Press, New York (1993); Grifin, A. M. & Grifin, H. G. (Ed.), Computer Analysis of Sequence Data: Part I, Human Press, New Jersey (1994); von Heinje, G., Sequence Analysis in Molecular Biology, Academic Press, New York (1987); Gribskov, M. & Devereux, J. (Ed.), Sequence Analysis Primer, M-Stockton Press, New York (1991)).

In addition, although the value of "identity" as described in the present description may be a value calculated using an identity search program known among persons with ordinary skill in the art unless specifically indicated otherwise, it is preferably the value calculated using the ClustalW Program supported by Mac Vector application software (Version 9.5, Oxford Molecular Ltd., Oxford, England).

The polynucleotide (nucleic acid, gene) of the present invention is that which "encodes" a protein of interest. Here, the term "encode" refers to expressing a protein of interest in a state in which it retains its activity. In addition, the term "encode" includes both the meanings of encoding a protein of interest in the form of a contiguous structural sequence (exon) and encoding a protein of interest mediated by an inclusion sequence (intron).

A gene having a natural base sequence is obtained by analyzing with a DNA sequencer as is subsequently described in the examples. In addition, DNA encoding an enzyme having a modified amino acid sequence can be synthesized using commonly used site-specific mutagenesis or PCR by using DNA based on a naturally-occurring base sequence. For example, a desired modified DNA fragment is obtained by obtaining a DNA fragment desired to be modified by treating naturally-occurring cDNA or genomic DNA with a restrictase, and carrying out site-specific mutagenesis or PCR using this as a template and using primers introduced with desired mutations. Subsequently, this DNA fragment introduced with a mutation is linked with a DNA fragment that encodes the other portions of a target enzyme.

Alternatively, in order to obtain DNA encoding an enzyme composed of a shortened amino acid sequence, an amino acid sequence longer than the target amino acid sequence, such as DNA encoding a full-length amino acid sequence, is cleaved by a desired restrictase, and in the case the resulting DNA fragment does not encode the entire target amino acid sequence, a DNA fragment composed of a sequence corresponding to the missing portion is synthesized and linked thereto.

In addition, by expressing the resulting polynucleotide using a gene expression system in *Escherichia coli* and yeast and then measuring the enzyme activity thereof, the polynucleotide can be confirmed to encode a protein having activity that transfers a sugar to the hydroxyl group at position 7 of a flavone, and particularly flavone 4'-glucoside. Moreover, a protein having activity that transfers a sugar to the hydroxyl group at position 7 of a polynucleotide product in the form of flavone, and particularly flavone 4'-glucoside, can be obtained by expressing that polynucleotide. Alternatively, a protein having activity that transfers a sugar to the hydroxyl group at position 7 of a flavone, and particularly flavone 4'-glucoside, can also be acquired by using an antibody to a polypeptide composed of the amino acid sequence set forth in SEQ ID NO: 2, and a polynucleotide that encodes a protein having activity that transfers a sugar to the hydroxyl group at position 7 of a flavone of other biological origin, and particularly flavone 4'-glucoside, can also be cloned using that antibody.

The present invention also relates to a vector, and particularly an expression vector, that contains (recombines) the aforementioned polynucleotide, and to a host that has been transformed by that vector.

A prokaryotic organism or eukaryotic organism can be used for the host. Examples of prokaryotic organisms include bacteria in the manner of bacteria belonging to the genus *Escherichia* such as *Escherichia coli*, bacteria belong to the genus *Bacillus* such as *Bacillus subtilis* and other bacteria commonly used as hosts. Examples of eukaryotic organisms that can be used include lower eukaryotic organisms such as eukaryotic microorganisms in the manner of fungi, yeasts and molds.

Examples of yeasts include *Saccharomyces* species microorganisms such as *Saccharomyces cerevisiae*, and examples of molds include *Aspergillus* species microorganisms such as *Aspergillus oryzae* or *Aspergillus niger* as well as *Penicillium* species microorganisms. Animal cells or plant cells can also be used as hosts, examples of animal cells used include mouse, hamster, monkey and human cells, and insect cells such as silkworm cells or adult silkworms per se are also used as hosts.

The expression vector of the present invention may further contain a polynucleotide selected from the group consisting of the following (f) to (j):

(f) a polynucleotide composed of the base sequence of SEQ ID NO: 3;

(g) a polynucleotide that hybridizes under stringent conditions with a polynucleotide composed of a base sequence complementary to the base sequence of SEQ ID NO: 3, and encodes a protein having activity that transfers a sugar to the hydroxyl group at position 4' of a flavone;

(h) a polynucleotide that encodes a protein composed of the amino acid sequence of SEQ ID NO: 4;

(i) a polynucleotide that encodes a protein that is composed of an amino acid sequence in which one or a plurality of amino acids have been deleted, substituted, inserted and/or added in the amino acid sequence of SEQ ID NO: 4, and has activity that transfers a sugar to the hydroxyl group at position 4' of a flavone; and, (j) a polynucleotide that encodes a protein that has an amino acid sequence having identity of 90% or more with the amino acid sequence of SEQ ID NO: 4, and has activity that transfers a sugar to the hydroxyl group at position 4' of a flavone. These polynucleotides encode proteins having activity that transfers a sugar to the hydroxyl group at position 4' of a flavone, and are described in detail in International Publication No. WO 2013/108794 (Patent Document 11).

In addition, the expression vector of the present invention contains an expression control region, such as a promoter, terminator or replication origin, that is dependent on the type of host into which it is introduced. A commonly used promoter is used for the promoter of a bacterial expression vector, and examples thereof include trc promoter, tac promoter and lac promoter, examples of yeast promoters that are used include glyceraldehyde triphosphate dehydrogenase promoter and PH05 promoter, and examples of mold promoters that are used include amylase promoter and trpC promoter. In addition, examples of promoters for use with animal cell hosts include viral promoters such as SV40 early promoter and SV40 late promoter.

Examples of promoters that constitutively express a polynucleotide in plant cells include the 35S RNA promoter of cauliflower mosaic virus, rd29A gene promoter, rbcS promoter and mac-1 promoter. In addition, a promoter of a gene that is specifically expressed in a tissue can be used to express a tissue-specific gene.

Preparation of an expression vector can be carried out in accordance with ordinary methods using restrictases or ligases and the like. In addition, host transformation by an expression vector can also be carried out in accordance with ordinary methods.

A target protein can be obtained by culturing, cultivating or growing a host that has been transformed by the aforementioned expression vector, and recovering and purifying from the culture or medium in accordance with an ordinary method such as filtration, centrifugal separation, cell lysing, gel permeation chromatography or ion exchange chromatography.

In the present description, although a description is provided of a gene that encodes a protein having activity that transfers a sugar to the hydroxyl group at position 7 of a flavone derived from Nemophilas, and particularly flavone 4'-glucoside, the polynucleotide according to the present invention is not limited to a gene derived from Nemophilas, but rather the origin of the gene that encodes a protein having activity that transfers a sugar to the hydroxyl group at position 7 of a flavone, and particularly flavone 4'-glucoside, may be a plant, animal or microorganism, and there are no particular limitations on the origin providing the resulting protein has activity that transfers a sugar to the hydroxyl group at position 4' of a flavone and can be used to modify flower color in plants.

The present invention also relates to a plant, progeny thereof, portion thereof or tissue thereof obtained by introducing an exogenous polynucleotide, which encodes a protein having activity that transfers a sugar to the hydroxyl group at position 7 of a flavone, and particularly flavone 4'-glucoside, into a plant and containing the polynucleotide in the plant. The plant portion or tissue can be in the form of a cut flower. Position 7 of a flavone, and particularly flavone 4'-glucoside, can be glycosylated or that glycosylation can be suppressed by using the polynucleotide according to the present invention that encodes a protein having activity that transfers a sugar to the hydroxyl group at position 7 of a flavone, and particularly flavone 4'-glucoside, thereby making it possible to alter flower color in a plant as a result thereof.

Moreover, in addition to the polynucleotide of the present invention, a polynucleotide may also be introduced into a plant that encodes a protein having activity that transfers a sugar to the hydroxyl group at position 4' of the aforementioned flavone. As a result, a flavone having hydroxyl groups added to both position 4' and position 7 can be efficiently biosynthesized in a plant.

At the current level of technology, technology can be used that enables a polynucleotide to be introduced into a plant followed by constitutively or tissue-specifically expressing that polynucleotide. Introduction of DNA into a plant can be carried out according to a method known among persons with ordinary skill in the art such as the *Agrobacterium* method, binary vector method, electroporation method, PEG method and particle gun method.

Examples of transformable plants include, but are not limited to, rose, carnation, *chrysanthemum*, snapdragon, cyclamen, orchid, tulip gentian, freesia, African daisy, gladiola, baby's breath, kalanchoe, lily, fancy geranium, geranium, *petunia*, torenia, tulip, flamingo flower, moth orchid, rice, barley, wheat, rapeseed, potato, tomato, poplar, banana, *eucalyptus*, sweet potato, soybean, alfalfa, rubin, corn, cauliflower and dahlia plants.

The present invention also relates to processed plants (processed cut flowers) using the aforementioned cut flowers. Here, examples of processed cut flowers include, but are not limited to, pressed flowers, preserved flowers, dry flowers and resin-sealed flowers that use these cut flowers.

In addition, a flavone having a sugar added to the hydroxyl group at position 7, and particularly a flavone having a sugar added to the hydroxyl groups at both position 4' and position 7, produced according to the production method of the present invention can be used in applications such as the production methods of foods, pharmaceuticals or cosmetics.

In the present invention, the expression of a target gene in a plant can be suppressed by a method such as the antisense method, co-suppression method or RNAi method. Although the method for suppressing expression of a target gene can be carried out by a method known among persons with ordinary skill in the art, examples thereof include the antisense RNA/DNA technique (Bioscience and Industry, 50, 322 (1992); Chemistry, 46, 681 (1991); Biotechnology, 9, 358 (1992); Trends in Biotechnology, 10, 87 (1992); Trends in Biotechnology, 10, 152 (1992); and, Cell Engineering, 16, 1463 (1997)), and the triple helix technique (Trends in Biotechnology, 10, 132 (1992)). For example, suppression of gene expression can be carried out using a single-stranded nucleic acid molecule comprising all or a portion of a nucleotide sequence identical to the antisense strand of the gene according to the present invention. This type of method is known as an antisense method. In the antisense method, expression of a target gene is suppressed by expressing RNA, having a sequence complementary to the gene for which expression is desired to be suppressed, at a high level. In this method, single-stranded RNA can be used that comprises the entire nucleotide sequence that is identical to the antisense strand of the polynucleotide (gene) according to the present invention. In addition, in the aforementioned method, single-stranded RNA can also be used that comprises a portion of a nucleotide sequence identical to the antisense strand of the gene according to the present invention. This partial single-stranded RNA is only required to be able to suppress expression of the gene according to the present invention, and although it can be suitably designed by a person with ordinary skill in the art, it is preferably specific for the gene according to the present invention, and the chain length thereof is preferably 5 nucleotides to 100 nucleotides, more preferably 5 nucleotides to 50 nucleotides and even more preferably 10 nucleotides to 20 nucleotides.

Suppression of gene expression is carried out using a single-stranded nucleic acid molecule comprising all or a portion of a nucleotide sequence identical to the sense strand of the gene according to the present invention. Namely, this sense single-stranded nucleic acid can be used to suppress expression of the gene according to the present invention in the same manner as the aforementioned antisense single-stranded nucleic acid. In this method, single-stranded RNA can be used that comprises the entire nucleotide sequence that is identical to the sense strand of the gene according to the present invention. In addition, in the aforementioned method, single-stranded RNA can be used that comprises a portion of a nucleotide sequence that is identical to the sense strand of the gene according to the present invention. This partial single-stranded RNA is only required to suppress expression of the gene according to the present invention, and although it can be suitably designed by a person with ordinary skill in the art, it is preferably specific for the gene according to the present invention, and the chain length thereof is preferably 5 nucleotides to 100 nucleotides, more preferably 5 nucleotides to 50 nucleotides and even more preferably 10 nucleotides to 20 nucleotides.

Moreover, suppression of gene expression is carried out using a double-stranded nucleic acid molecule comprising all or a portion of a nucleotide sequence identical to the gene according to the present invention. For example, an antisense or sense single-stranded nucleic acid of the gene according to the present invention can be expressed in an angiosperm by using this double-stranded nucleic acid molecule. The double-stranded nucleic acid molecule according to the present invention is preferably DNA, and the chain length and specific nucleotide sequence thereof correspond to the chain length and nucleotide sequenced of the target single-stranded nucleic acid molecule. For example, in the case of expressing the aforementioned antisense single-stranded nucleic acid, the double-stranded nucleic acid molecule according to the present invention contains the antisense strand of the gene according to the present invention as the encoded strand. In addition, in the case of expressing the aforementioned sense single-stranded nucleic acid, the double-stranded nucleic acid molecule according to the present invention contains the sense strand of the gene according to the present invention as the encoded strand.

A double-stranded nucleic acid molecule can be expressed in a plant using a method known among persons with ordinary skill in the art. For example, a double-stranded nucleic acid molecule can be expressed by cultivating a plant body obtained by introducing an expression vector containing a promoter, the double-stranded nucleic acid molecule according to the present invention and a transcription terminator and the like into a target plant. Introduction of the expression vector into the plant can be carried out by a method known among persons with ordinary skill in the art, such as the *Agrobacterium* method, binary vector method, electroporation method, PEG method or particle gun method.

Another example of a method for suppressing gene expression using a nucleic acid molecule according to the present invention is the co-suppression method. In this method, sense double-stranded DNA having the entire nucleotide sequence of the gene according to the present invention is introduced into a target plant. As a result, the sense single-stranded RNA according to the present invention is expressed and expression of the gene is then drastically suppressed by this RNA (Plant Cell, 9, 1357-1368, 1997).

According to the present invention, a novel polynucleotide is provided that encodes a protein having activity that transfers a sugar to the hydroxyl group at position 7 of a flavone (and particularly flavone 4'-glucoside). A protein having activity that transfers a sugar to the hydroxyl group at position 7 of a flavone (and particularly flavone 4'-glucoside) can be produced by expressing the polynucleotide of the present invention in a suitable host cell. According to the present invention, a protein having activity that transfers a sugar to the hydroxyl group at position 7 of a flavone (and particularly flavone 4'-glucoside) can be used to modify flower color by expressing constitutively or tissue-specifically in a plant. In addition, according to the present invention, a method for producing a flavone having a sugar added to the hydroxyl group at position 7, and particularly a flavone having a sugar added to the hydroxyl groups at both position 4' and position 7, and a composition containing a flavone obtained according to that production method, are provided.

EXAMPLES

The following provides a detailed explanation of the present invention in accordance with examples thereof.

Example 1: Detection of Activity that Transfers Hydroxyl Groups to Position 4' and Position 7 in Flower Petals of *Nemophila menziesii*

Flower petals of *Nemophila menziesii* were harvested at the development stages defined below, frozen with liquid nitrogen, and stored in a freezer at −80° C.

Stage 1: Tightly closed buds without color (approx. 2 to 5 mm)

Stage 2: Colored tightly closed buds (approx. 2 to 5 mm)

Stage 3: Colored closed buds with the sepals beginning to open (approx. 5 to 10 mm)

Stage 4: Buds with the petals beginning to open (approx. 10 to 15 mm)

Stage 5: Completely opened petals

<Preparation of *Nemophila menziesii* Flower Petal Extract>

Flavone glycosyltransferase activity is expected to be detected in stages 1 and 2 of the flower petals prior to biosynthesis of anthocyanin. Therefore, flower petal extracts were prepared using stage 1 and stage 2 flower petals. 250 mg of a flower petal sample (125 mg each of stage 1 and stage 2 flower petals stored at −80° C.) were crushed with a mortar and pestle in liquid nitrogen followed by the addition of 2.0 ml of extraction buffer (composition: 100 mM potassium phosphate buffer (pH 7.5), 1 mM dithiothreitol (DTT), 50 mg/ml of polyvinylpyrrolidone 40 and 100 mg/ml of sucrose) and suspending the sample therein. The resulting suspension was centrifuged (10,000 rpm, 4° C., 10 minutes) followed by the addition of ammonium sulfate to the recovered supernatant to 30% of the saturated concentration. After stirring for 1 hour at 4° C., the suspension was centrifuged (10,000 rpm, 4° C., 10 minutes) followed by recovery of the supernatant. Ammonium sulfate was added to the resulting supernatant to 70% of the saturated concentration followed by stirring for 1 hour at 4° C. and centrifuging (10,000 rpm, 4° C., 10 minutes) to obtain a precipitate. This precipitate was dissolved in 500 µl of elution buffer (composition: 2.5 mM Tris-HCl (pH 7.5), 1 mM DTT, 10 µM amidinophenyl-methanesulfonyl fluoride hydrochloride (APMSF)) and then desalted using the Sephadex G-25 DNA Grade NAP-5 Column (GE Healthcare Corp.) to remove the ammonium sulfate. This liquid was used as "flower petal extract". The Avanti HP-26XP centrifuge (rotor: JA-2, Beckman Coulter Inc.) was used for centrifugation.

<Measurement of Enzyme Activity Using *Nemophila menziesii* Flower Petal Extract>

A reaction solution prepared by mixing 40 µl of flower petal extract, 2 µl of 50 mM UDP-glucose, 20 µl of 1 M Tris-HCl (pH 7.5) and 5 µl of 1 mM apigenin (dissolved in 50% aqueous acetonitrile solution containing 0.1% TFA) on ice and bringing to reaction volume of 200 µl with water was stored for 20 minutes at 30° C. Subsequently, 200 µl of stop buffer (90% aqueous acetonitrile solution containing 0.1% TFA) were added to stop the reaction followed by analyzing the reaction solution by high-performance liquid chromatography (Prominence, Shimadzu Corp.). Flavone was detected at 330 nm using the Shimadzu PDA SPD-M10AVP for the detector. The Shim-Pack ODS column (150 mm×4.6 mm, Shimadzu Corp.) was used for the column. A liquid A (0.1% aqueous TFA solution) and a liquid B (90% aqueous methanol solution containing 0.1% TFA) were used for elution. Elution was carried out for 10 minutes at a linear concentration gradient from an 8:2 mixture of the two solutions to a 3:7 mixture of the two solutions followed by eluting for 6 minutes using a 3:7 mixture of the two solutions. The flow rate was 0.6 ml/min. A reaction solution obtained by carrying out the enzyme reaction under the same conditions using a flower petal extract obtained by subjecting the flower petal extract to heat treatment for 20 minutes at 100° C. was used as a control.

As a result, in addition to flavone demonstrating the same retention time and absorption maximum as a purified apigenin 4',7'-glucoside product and apigenin 7-glucoside standard, flavone demonstrating retention time close to that of apigenin 7-glucoside was biosynthesized (see FIG. 1). Peaks other than apigenin were not detected when the enzyme reaction was carried out without adding UDP-glucose.

Figure 2:
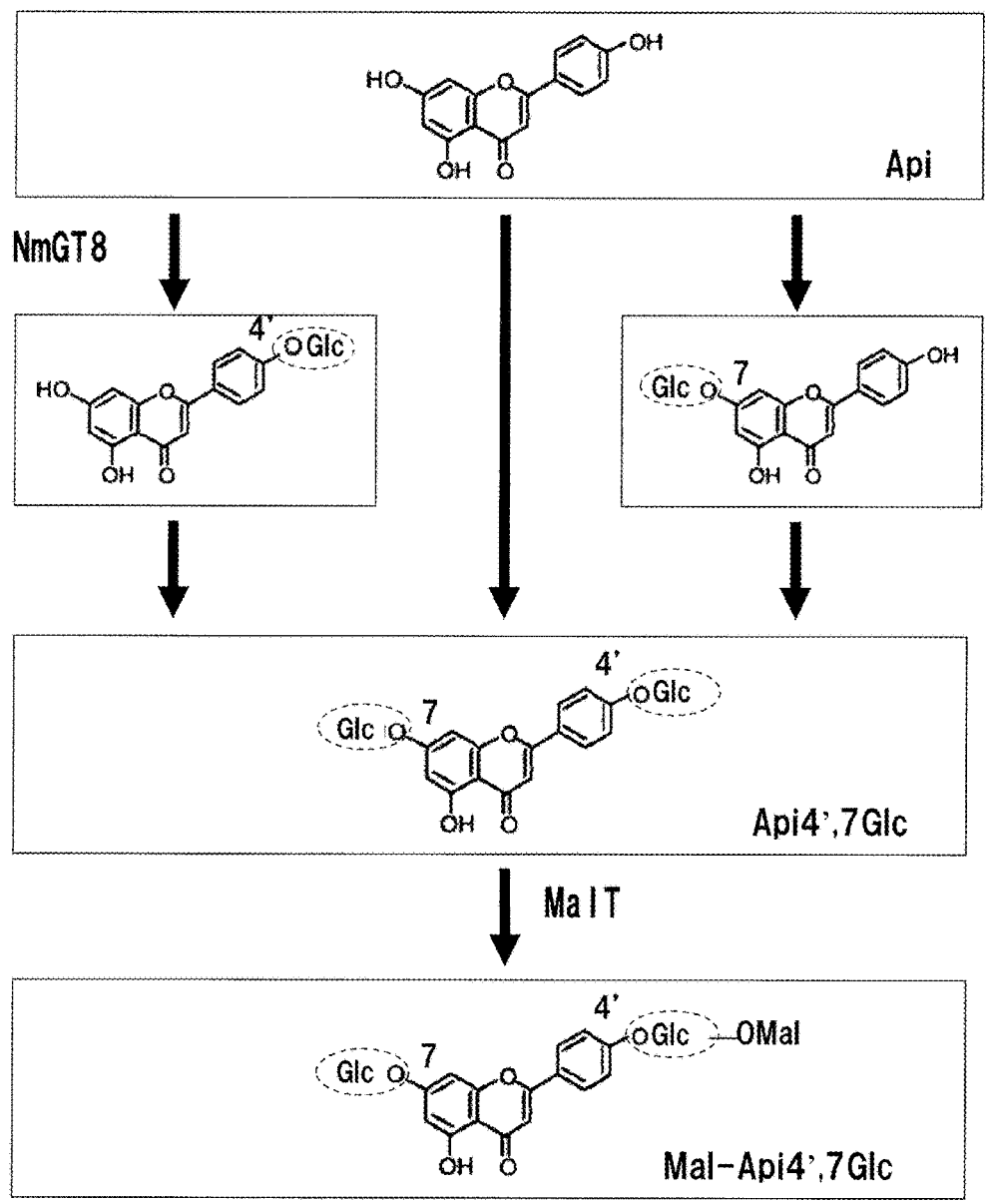
FIG. 2 is a drawing for explaining the biosynthetic pathway of apigenin 4',7'-diglucoside.

Example 2: Determination of Retention Time and Absorption Maximum of Apigenin 4'-Glucoside When considering the biosynthetic pathway of apigenin 4',7-diglucoside in *Nemophila menziesii* flower petals, apigenin 4'-glucoside and apigenin 7-glucoside are expected to be biosynthesized as intermediate products during the course of biosynthesis of apigenin 4',7-diglucoside (see FIG. 2). On the basis thereof, the flavone demonstrating a retention time close to that of apigenin 7-glucoside detected in Example 1 was judged to be apigenin 4'-glucoside (see FIG. 1). The retention time and absorption maximum of apigenin 4'-glucoside were able to be determined.

According to these results, a protein having activity that respectively transfers a sugar to hydroxyl groups at position 4' and position 7 of flavone that is dependent on UDP-glucose was clearly determined to be present. There are thought to be three possible candidates for the biosynthetic pathway of flavone 4',7-diglucoside, consisting of a pathway by which glycosylation of the hydroxyl groups at position 4' and position 7 of the flavone is carried out by a single enzyme, a pathway by which glycosylation of the hydroxyl group at position 7 of the flavone is carried out after having carried out glycosylation of the hydroxyl group at position 4', and a pathway by which glycosylation of the hydroxyl group at position 4' of the flavone is carried out after having carried out glycosylation of the hydroxyl group at position 7 (see FIG. 2). Previously, NmGT3 and NmGT4 have been acquired as genes that encode a protein having activity that transfers a sugar to the hydroxyl group at position 4' and/or position 7 of a flavone (Patent Document 12), while NmGT8 has been acquired as a gene that encodes a protein having activity that transfers a sugar to the 4' position of a flavone (Patent Document 11, SEQ ID NO: 3).

Example 3: Acquisition of Candidate Genes Encoding Protein Having Activity that Transfers Sugar to Hydroxyl Group at Position 7 of Flavone 4'-Glucoside <Isolation of Total RNA>

Total RNA was isolated from the stage 1 and stage 2 flower petals of *Nemophila menziesii* using the Plant RNAeasy Kit (Qiagen Corp.) in accordance with the manufacturer's recommended protocol.

<Expression Analysis of cDNA Derived from *Nemophila menziesii* Flower Petals>

A reverse transcription reaction was carried out on 30 µg of total RNA derived from *Nemophila menziesii* flower petals followed by the production of an equalized DNA library. After amplifying a clone of the resulting library by emulsion PCR, the base sequence was determined with the Genome Sequencer FLX (Roche Diagnostics K.K.). Sequences were extracted from the resulting sequence data that demonstrated identity with the gene sequence of gentian anthocyanin 3'-glucosyltransferase. Candidate genes encoding glycosyltransferase were obtained by translating these sequences into amino acid sequences and assembling.

Example 4: Acquisition of Full-Length cDNA of Candidate Genes Encoding Protein Having Activity that Transfers Sugar to Hydroxyl Group at Position 7 of Flavone 4'-Glucoside 30 types of glucosyltransferase candidate gene sequences were obtained in Example 3. Experiments were conducted on 20 of those genes (NmGT10 to NmGT29) in order to acquire full-length cDNA sequences.

Acquisition of full-length cDNA sequences was carried out using the GeneRacer Kit (Invitrogen Inc.) in accordance with the manufacturer's recommended protocol. A region specific to that clone was selected from among the partial cDNA sequences obtained in Example 3, a RACE primer was designed based on the sequence of that region, and a 5',3'-terminating sequence was acquired by RACE PCR. Primers for amplifying the full-length cDNA were designed based on this sequence, and a PCR reaction was carried out at a reaction volume of 50 μl using *Nemophila menziesii* cDNA as template and using KOD-Plus Polymerase (Toyobo Co, Ltd.) in accordance with the manufacturer's recommended protocol (by repeating 30 cycles consisting holding for 2 minutes at 94° C., for 15 seconds at 94° C., for 30 seconds at 55° C. and for 2 minutes at 68° C., followed by holding at 4° C.). *Nemophila menziesii* cDNA was synthesized using SuperScript II Reverse Transcriptase (Invitrogen Inc.) and using the total RNA isolated in Example 2 as template in accordance with the manufacturer's recommended protocol. Plasmids containing the entire length of NmGT gene (pET SUMO-NmGT10 to pET SUMO-NmGT29) were acquired using these PCR products and using the pET SUMO TA Cloning Kit (Invitrogen Inc.) in accordance with the manufacturer's recommended protocol. The base sequences inserted into the plasmids were analyzed, and full-length cDNA sequences were acquired from the candidate genes encoding protein having activity that transfers a sugar to the hydroxyl group at position 7 of flavone 4'-glucoside (NmGT10 to NmGT29). The pET SUMO-NmGT10 to pET SUMO-NmGT29 were used as *E. coli* expression constructs in Example 5 and subsequent examples.

Example 5: Experiment for Measuring Enzyme Activity of Protein Candidates Having Activity that Transfers Sugar to Hydroxyl Group at Position 7 of Flavone 4'-Glucoside (Case of Using Crude Enzyme)

<Expression of Glycosyltransferase in *E. coli*> pET SUMO-NmGT10 to pET SUMO-NmGT29 were introduced into *E. coli* strain BL2 using One Shot BL21 (DE3) (Invitrogen Inc.) in accordance with the manufacturer's recommended protocol to acquire transformed *E. coli*. The *E. coli* were cultured using the Overnight Express Auto-induction System 1 (Novagen Inc.) in accordance with the manufacturer's recommended protocol. The transformed *E. coli* were cultured in 2 ml of prepared culture broth at 37° C. until the OD600 value reached 0.5 (about 4 hours). This *E. coli* culture broth was added to a 50 ml of culture broth as pre-culture broth followed by final culturing overnight at 25° C.

After having been cultured overnight, the *E. coli* culture broth was centrifuged (3,000 rpm, 4° C., 15 minutes), the harvested bacterial cells were suspended in 5 ml of sonic buffer (composition: 2.5 mM Tris-HCl (pH 7.0), 1 mM dithiothreitol (DTT), 10 IAM amidinophenylmethanesulfonyl fluoride hydrochloride (APMSF)), and the *E. coli* were crushed by ultrasonic treatment followed by centrifuging (15,000 rpm, 4° C., 10 minutes) and recovering the supernatant. The supernatant was used as a crude enzyme solution. The Avanti HP-26XP centrifuge (rotor: JA-2, Beckman Coulter Inc.) was used for centrifugation.

<Measurement of Enzyme Activity>

A reaction solution prepared by mixing 80 μl of crude enzyme solution, 2 μl of 50 mM UDP-glucose, 20 μl of 1 M Tris-HCl (pH 7.5) and 1 μl of 2 mM apigenin 4'-glucoside (dissolved in 50% aqueous acetonitrile solution containing 0.1% TFA) on ice and bringing to reaction volume of 200 μl with water was stored for 30 minutes at 30° C. Subsequently, 200 μl of stop buffer (90% aqueous acetonitrile solution containing 0.1% TFA) were added to stop the reaction followed by analyzing the reaction solution by high-performance liquid chromatography (Prominence, Shimadzu Corp.). Flavone was detected at 330 nm using the Shimadzu PDA SPD-M10AVP for the detector. The Shim-Pack ODS column (150 mm×4.6 mm, Shimadzu Corp.) was used for the column. A liquid A (0.1% aqueous TFA solution) and a liquid B (90% aqueous methanol solution containing 0.1% TFA) were used for elution. Elution was carried out for 10 minutes at a linear concentration gradient from an 8:2 mixture of the two solutions to a 3:7 mixture of the two solutions followed by eluting for 6 minutes using a 3:7 mixture of the two solutions. The flow rate was 0.6 ml/min. A reaction solution obtained by carrying out the enzyme reaction under the same conditions using a crude enzyme solution of *E. coli* introduced with pET SUMO vector not containing an insert was used as a control.

As a result, peaks other than substrate were observed for NmGT22.

Descriptions of NmGT22 (SEQ ID NO: 1) and its homolog in the form of NmGT22-II (SEQ ID NO: 5) are provided starting with Example 6.

Example 6: Experiment for Measuring Enzyme Activity of Protein Candidates Having Activity that Transfers Sugar to Hydroxyl Group at Position 7 of Flavone 4'-Glucoside (Case of Using Purified Enzyme Following Addition of His-Tag)

<Expression of Glucosyltransferase in *E. coli* and Protein Purification>

*E. coli* strain BL2 introduced with pET SUMO-NmGT22 described in Example 5 was cultured using the Overnight Express Auto-induction System 1 (Novagen Inc.) in accordance with the manufacturer's recommended protocol. The transformed *E. coli* were cultured in 8 ml of prepared culture broth at 37° C. until the OD600 value reached 0.5 (about 4 hours). This *E. coli* culture broth was added to 200 ml of a culture broth as pre-culture broth followed by final culturing overnight at 25° C.

After having been cultured overnight, the *E. coli* culture broth was centrifuged (1,000×g, 4° C., 10 minutes), the harvested bacterial cells were suspended in 20 ml of extract (composition: buffer solution (300 mM KCl, 50 mM $KH_2PO_4$, 5 mM imidazole) (pH 8.0), 10 μM amidinophenylmethanesulfonyl fluoride hydrochloride (APMSF)), and the *E. coli* were crushed by ultrasonic treatment followed by centrifuging (1,400×g, 4° C., 20 minutes) and recovering the supernatant. The supernatant was passed through a 0.45 μm filter and subjected to His-Tag purification using Profinia (Bio-Rad Corp.) in accordance with the manufacturer's recommended protocol. The resulting purified protein solution was centrifuged (7,500×g, 4° C., 15 minutes) using a centrifugal filter unit (Ultracel-10K, Amicon Ultra), and the concentrated protein solution was used as "NmGT-22 Protein Solution". The Avanti HP-26XP centrifuge (rotor: JA-2, Beckman Coulter Inc.) was used for centrifugation.

<Measurement of Enzyme Activity>

A reaction solution prepared by mixing 10 μl of protein solution, 2 it of 50 mM UDP-glucose, 10 μl of 1 M Tris-HCl (pH 7.5) and 1 µl of 2 mM apigenin 4'-glucoside (dissolved in 50% aqueous acetonitrile solution containing 0.1% TFA) on ice and bringing to reaction volume of 100 µl with water was held for 20 minutes at 30° C. Subsequently, 100 µl of stop buffer (90% aqueous acetonitrile solution containing 0.1% TFA) were added to stop the reaction followed by analyzing the reaction solution by high-performance liquid chromatography (Prominence, Shimadzu Corp.). Flavone was detected at 330 nm using the Shimadzu PDA SPD-M10AVP for the detector. The Shim-Pack ODS column (150 mm×4.6 mm, Shimadzu Corp.) was used for the column. A liquid A (0.1% aqueous TFA solution) and a liquid B (90% aqueous methanol solution containing 0.1% TFA) were used for elution. Elution was carried out for 10 minutes at a linear concentration gradient from an 8:2 mixture of the two solutions to a 3:7 mixture of the two solutions followed by eluting for 6 minutes using a 3:7 mixture of the two solutions. The flow rate was 0.6 ml/min.

Figure 3:
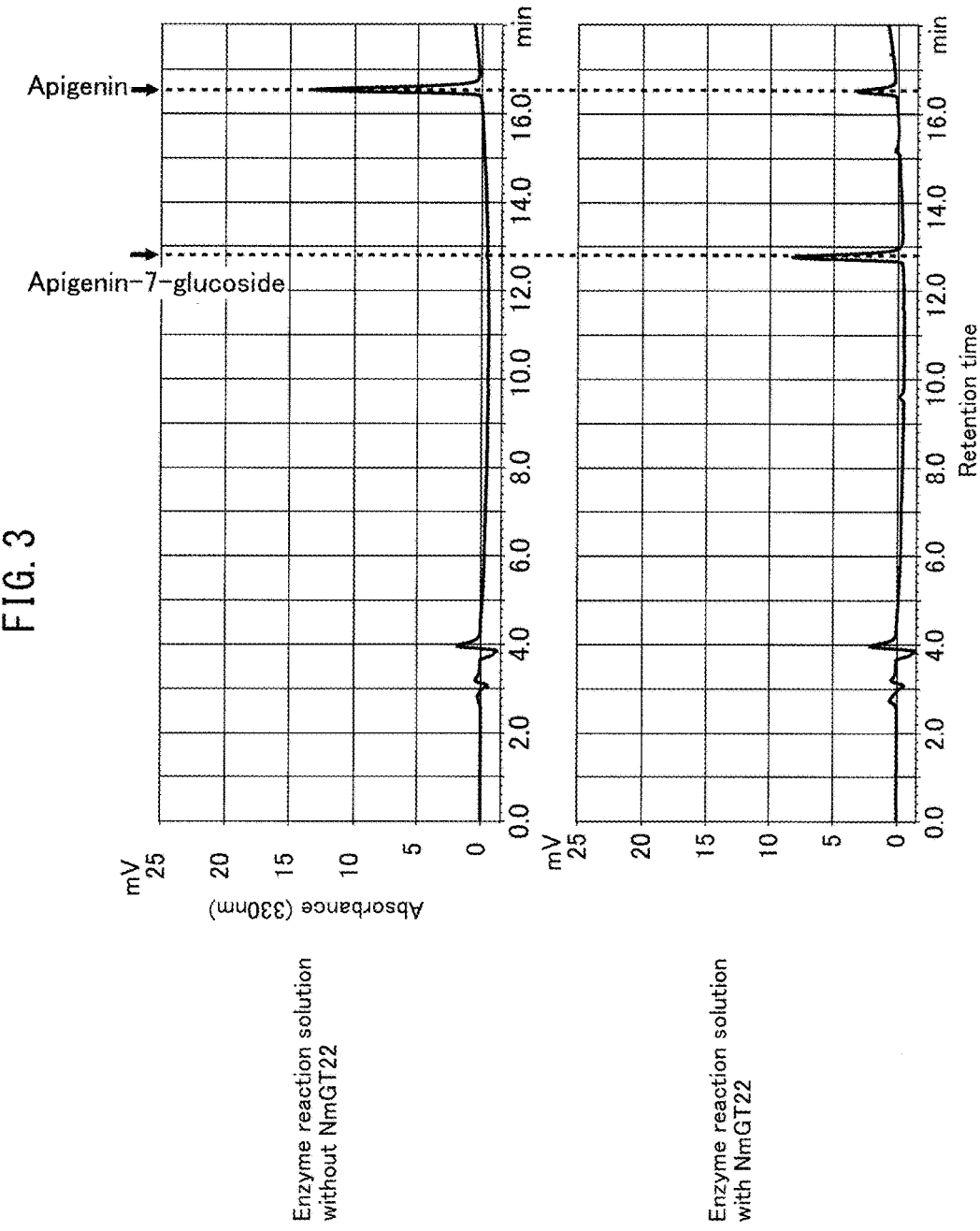
FIG. 3 is a high-performance liquid chromatogram of a liquid in which a solution of NmGT22 protein and apigenin underwent an enzymatic reaction.
Figure 4:
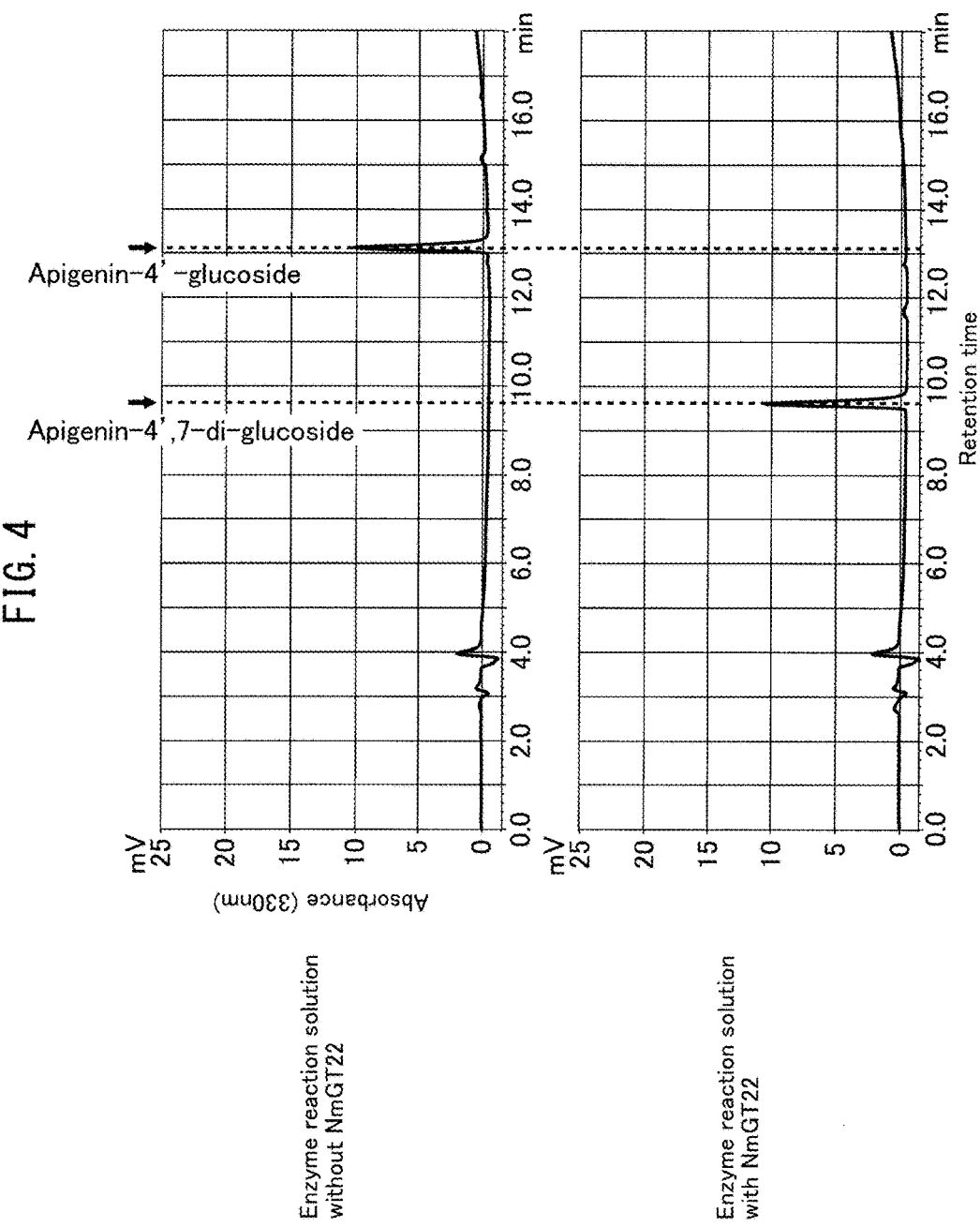
FIG. 4 is a high-performance liquid chromatogram of a liquid in which a solution of NmGT22 protein and apigenin 4'-glucoside underwent an enzymatic reaction.

As a result, flavone was synthesized that demonstrated the same retention time and absorption maximum as those of apigenin 4',7-diglucoside. The reaction rate (percentage of transformed substrate) was 100% (see FIGS. 4 and 6). Luteolin 4',7-diglucoside was synthesized in the case of having carried out the enzyme reaction under the same reaction conditions using 2 mM luteolin 4'-glucoside (dissolved in 50% aqueous acetonitrile solution containing 0.1% TFA) for the substrate (FIG. 6). On the other hand, apigenin 4',7-diglucoside was not synthesized while apigenin 7-glucoside was synthesized in the case of having carried out the enzyme reaction under the same reaction conditions using 2 mM apigenin (dissolved in 50% aqueous acetonitrile solution containing 0.1% TFA) for the substrate. The reaction rate in this case was 77.16% (see FIGS. 3 and 6). Similarly, luteolin 4',7-diglucoside was not synthesized while luteolin 7-glucoside was synthesized in the case of having carried out the enzyme reaction under the same conditions using 2 mM luteolin (dissolved in 50% aqueous acetonitrile solution containing 0.1% TFA) for the substrate. The reaction rate in this case was 99.07% (FIG. 6). Moreover, apigenin 4',7-diglucoside was only synthesized in a trace amount in the case of having carried out the enzyme reaction under the same reaction conditions using 2 mM apigenin 7-glucoside (dissolved in 50% aqueous acetonitrile solution containing 0.1% TFA) for the substrate, and the reaction rate in this case was only 2.69% (see FIGS. 5 and 6). Similarly, luteolin 4',7-diglucoside was only synthesized in a trace amount in the case of having carried out the enzyme reaction under the same reaction conditions using 2 mM luteolin 7-glucoside (dissolved in 50% aqueous acetonitrile solution containing 0.1% TFA) for the substrate, and the reaction rate in this case was 16.10% (FIG. 6). Moreover, when reactivity to various types of flavone compounds described in FIG. 6 (pelargonidin, pelargonidin 3-glucoside, cyanidin, cyanidin 3-glucoside, delphinidin, delphinidin 3-glucoside, myricetin, tricetin, kaempferol, kaempferol 3-glucoside, quercetin, quercetin 3-glucoside, myricetin and isovitexin) along with betanidin was investigated, NmGT22 protein selectively glycosylated the hydroxyl group at position 7 of flavones in the manner of apigenin 4'-glucoside, luteolin 4'-glucoside, apigenin and luteolin, and was clearly determined to demonstrate high substrate specificity. Activity was clearly determined to be the most potent when the substrate consisted of a flavone in which a sugar had been transferred to the hydroxyl group at position 4' (see FIG. 6).

In addition, base sequence and amino acid sequence identity were analyzed between NmGT22 and known glycosyltransferases. When NmGT22 was compared with glucosyltransferases derived from the same *Nemophila menziesii*, amino acid sequence identity between NmGT22 and NmGt3, between NmGT22 and NmGT4 and between NmGT22 and NmGT8 were 24%, 25% and 24%, respectively. In addition, amino acid sequence identity between NmGT22 and *Pyrus communis*-derived glucosyltransferase in the form of PcF7GT was 32% (see Table 1). Although the previously identified glucosyltransferase demonstrating the highest identity with NmGT22 was VvgGT2 (GenBank Accession No. JN164680), amino acid sequence identity was only 62% (see Table 1 and FIG. 7). The ClustalW Program supported by Mac Vector application software (Version 9.5, Oxford Molecular Ltd., Oxford, England) was used for this analysis.

TABLE 1

| | Identity with NmGT22 (%) | | |
|---|---|---|---|
| | Function | Base Sequence | Amino Acid Sequence |
| NmGT3 | F4',7-GT (does not function in plants) | 45 | 24 (+20) |
| NmGT4 | F4',7-GT (does not function in plants) | 47 | 25 (+18) |
| NmGT8 | F4'-GT | 45 | 24 (+20) |
| VvgGT2 | GT adding sugar to hydroxybenzoic acid and cinnamic acid | 65 | 62 (+16) |
| PcF7GT | Flavonoid7-GT | 48 | 32 (+16) |

Based on these results as well, NmGT22 is presumed to demonstrate a function in plants that differs from that of known glycosyltransferases. In actuality, NmGT3 and NmGT4 do not have activity in plants that transfers a sugar to the hydroxyl group at position 4' and/or position 7 in a flavone. Although NmGT8 has activity that transfers a sugar to the hydroxyl group at position 4' of a flavone, it does not have activity that transfers a sugar to the hydroxyl group at position 7. Although VvgGT2 has a function that adds a sugar to hydroxybenzoic acid or cinnamic acid in grapes, it does not have activity that specifically transfers a sugar to the hydroxyl group at position 7 of a flavone in the manner of NmGT22. Although PcF7GT has activity that transfers a sugar to the hydroxyl group at position 7 of a type of flavonoid in the form of eriodictyol, flavones are not present in pears and the glycosyltransferase activity thereof on flavone 4'glucoside is not known. Accordingly, it is thought to have substrate specificity that is clearly different from NmGT22, which demonstrates selective activity particularly with respect to flavone 4'-glucoside. Moreover, although NmGT22 also has activity that specifically transfers a sugar to the hydroxyl group at position 5 of anthocyanin 3-glycoside (see FIG. 6), PcF7GT has been reported to not have a function that transfers a sugar to the hydroxyl group at position 5 of a flavonoid (Non-Patent Document 12).

Figure 8:
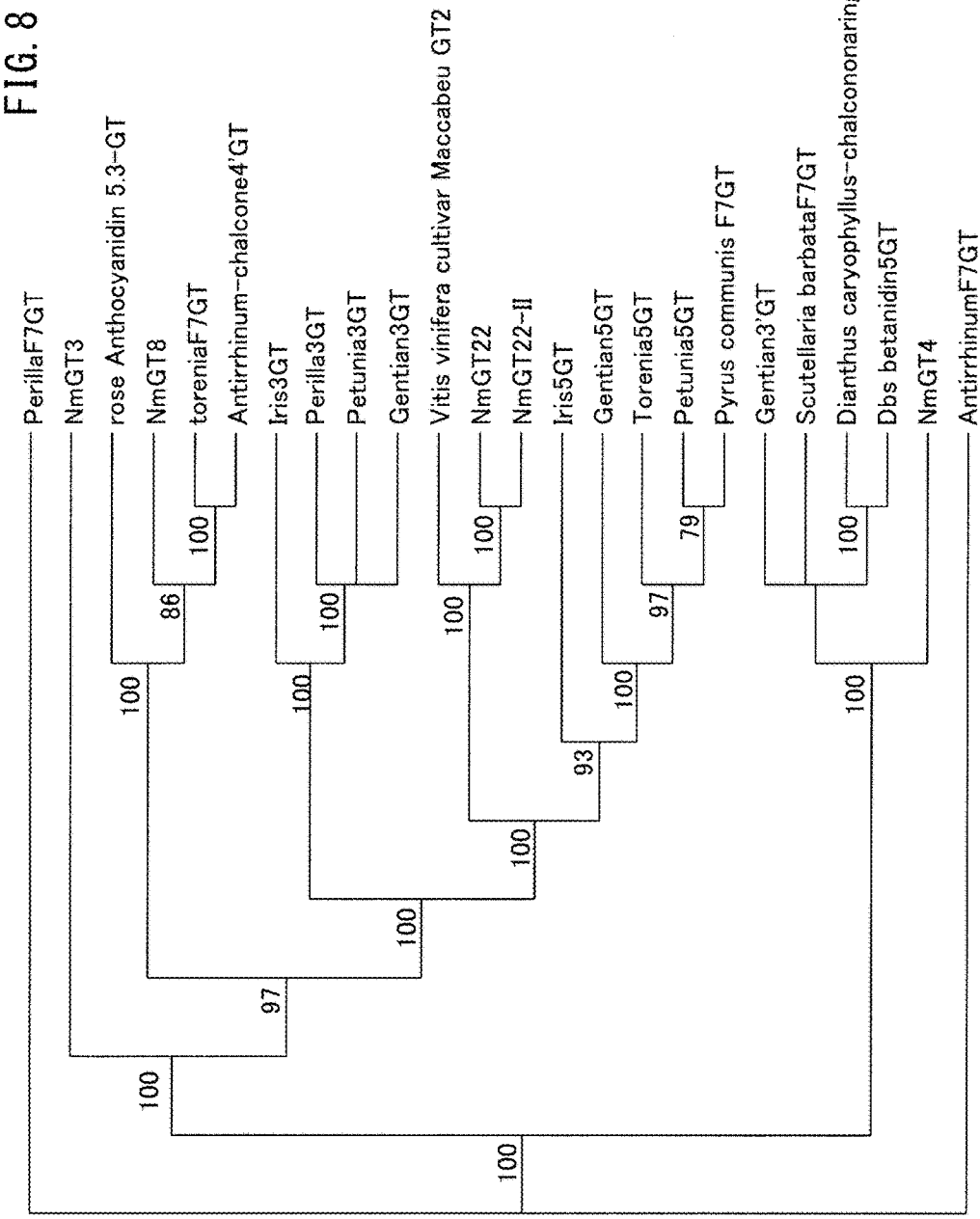
FIG. 8 is a phylogenetic tree that uses the relationships of the NmGT22 of the present invention and its homolog (NmGT22-II) with various previously described enzymes as indices.

In addition, FIG. 8 shows a phylogenetic tree that uses the relationships of the NmGT22 of the present invention with the various previously described enzymes as indices.

Example 7: Expression of NmGT22 Gene in Tabacco BY-2 Cells

The presence or absence of glycosylation of the hydroxyl groups at position 4' and position 7 of a flavone in BY-2 cells in which NmGT22 and NmGT8 were co-expressed was evaluated in order to confirm that the NmGT22 gene of the present invention encodes a protein having activity that transfers a sugar to the hydroxyl group at position 7 of flavone 4'-glucoside in plants.

A binary vector pSPB6261 was constructed and introduced into a plant in order to co-express NmGT22 and NmGT8 in the plant.

In the introduced binary vector pSPB6261, pBINPLUS (van Engel et al., Transgenic Research 4, p. 288) was used for the basic skeleton, and E1235S promoter (Mitsuhara et al., (1996) Plant Cell Physiol. 37, p. 49) was used for the promoter that expresses NmGT22 gene and NmGT8 gene, and HSP terminator (Plant Cell Physiol. (2010) 51, 328-332) was used for the terminator.

Transformation of the BY-2 cells was carried out according to the method described below. First, the BY-2 cells were cultured in 100 ml of BY-2 culture broth medium (composition: 10 types of inorganic compounds (1.65 g/L of $NH_4NO_3$, 1.9 g/L of $KNO_3$, 170 mg/L of $KH_2PO_4$, 6.2 mg/L of $H_3BO_2$, 22.3 mg/L of $MnSO_4.4H_2O$, 8.6 mg/L of $ZnSO_4.7H_2O$, 0.83 mg/L of KI, 0.25 mg/L of $Na_2MoO_4.2H_2O$, 0.025 mg/L of $CuSO_4.5H_2O$, 0.025 mg/L of $CoCl_2.6H_2O$), 440 mg/L of $CaCl_2$—$H_2O$, 370 mg/L of $MgSO_4.7H_2O$, 42.1 mg/L of Fe-EDTA, 30 g/L of sucrose, 100 mg/L of myo-inositol, 1 mg/L of thiamine-HCl, 0.2 mg/L of 2,4-dichlorophenoxyacetate) (pH 5.7), and the cells were cultured at 27° C. until the OD550 value reached 1.3 (about 3 days). 50 µl of *Agrobacterium* solution introduced with pSPB6261, which was cultured at 28° C. in 5 ml of YEP medium (composition: 10 g/L of Bacto™ Yeast Extract, 10 g/L of Bacto™ Peptone, 5 g/L of NaCl) (pH 7.0) until the OD550 value reached 1.7, and 1.5 µl of 20 mM acetosyringone were added to 3 ml of this BY-2 culture broth followed by additionally culturing for two and a half days at 27° C. After culturing for two and a half days, the co-culture broth of BY-2 cells and *Agrobacterium* was centrifuged (800 rpm, 15° C., 1 minute) followed by the addition of 10 ml of washing medium (composition: 10 types of inorganic compounds (1.65 g/L of $NH_4NO_3$, 1.9 g/L of $KNO_3$, 170 mg/L of $KH_2PO_4$, 6.2 mg/L of $H_3BO_3$, 22.3 mg/L of $MnSO_4.4H_2O$, 8.6 mg/L of $ZnSO_4.7H_2O$, 0.83 mg/L of KI, 0.25 mg/L of $Na_2MoO_4.2H_2O$, 0.025 mg/L of $CuSO_4.5H_2O$, 0.025 mg/L of $CoCl_2.6H_2O$), 440 mg/L of $CaCl_2$—$H_2O$, 370 mg/L of $MgSO_4.7H_2O$, 42.1 mg/L of Fe-EDTA, 30 g/L of sucrose, 100 mg/L of myo-inositol, 1 mg/L of thiamine-HCl, 0.2 mg/L of 2,4-dichlorophenoxyacetate, disodium carbenicillin) (pH 5.7) to the cell layer obtained by removing the supernatant to suspend the cells. This suspension procedure was repeated five times to remove the *Agrobacterium* from the co-culture broth of BY-2 cells and *Agrobacterium*. The Himac CF16RX (Hitachi Ltd.) (rotor: T4SS31) was used for centrifugation. 1 ml of this BY-2 culture broth was inoculated into selective medium containing kanamycin (composition: 10 types of inorganic compounds (1.65 g/L of $NH_4NO_3$, 1.9 g/L of $KNO_3$, 170 mg/L of $KH_2PO_4$, 6.2 mg/L of $H_3BO_3$, 22.3 mg/L of $MnSO_4.4H_2O$, 8.6 mg/L of $ZnSO_4.7H_2O$, 0.83 mg/L of KI, 0.25 mg/L of $Na_2MoO_4.2H_2O$, 0.025 mg/L of $CuSO_4.5H_2O$, 0.025 mg/L of $CoCl_2.6H_2O$), 440 mg/L of $CaCl_2.H_2O$, 370 mg/L of $MgSO_4.7H_2O$, 42.1 mg/L of Fe-EDTA, 30 g/L of sucrose, 100 mg/L of myo-inositol, 1 mg/L of thiamine-HCl, 0.2 mg/L of 2,4-dichlorophenoxyacetate, disodium carbenicillin, kanamycin) (pH 5.7) followed by selecting transgenic BY-2 cells introduced with NmGT22 and NmGT8.

<Analysis of Expression of NmGT22 Gene in BY-2 Cells>

Expression of NmGT22 gene was analyzed using the selected BY-2 cell mass. Total RNA was acquired by isolating according to the method described in Example 3, and synthesis of cDNA was carried out according to the method described in Example 4. The reverse transcription PCR reaction was carried out at a reaction volume of 30 µl using the cDNA as template and using ExTaq Polymerase (Takara Bio Inc.) in accordance with the manufacturer's recommended protocol (by repeating 25 cycles consisting holding for 2 minutes at 94° C., 1 minute at 94° C., 1 minute at 55° C. and for 2 minutes at 72° C., followed by holding at 4° C.). Primers were designed so as to specifically amplify the full length of NmGT22 cDNA (forward primer: ATGGAATG-CAAAAATCCAGATTC, reverse primer: CTAGG-TAATAAATCTGAAATTATTG). Since a 1432 b band corresponding to the full-length cDNA was detected when the reaction product was analyzed by agarose gel electrophoresis, NmGT22 gene was confirmed to have been transcribed in BY-2 cells.

<Analysis of Function of NmGT22 in BY-2 Cells>

Expression was similarly analyzed for NmGT8 (forward primer: ATGGAGAAAAAAACTATT, reverse primer: CTATTTCCAACCATCCAG, full-length cDNA: 1425 b) in order to select a BY-2 cell line in which transcription products are synthesized for full-length NmGT8 cDNA and full-length NmGT22 cDNA. An experiment was conducted that the BY-2 cell line in which full-length transcripts of NmGT8 and NmGT22 cDNA were confirmed was fed with apigenin which is a substrate of NmGT8 and NmGT22.

Transgenic BY-2 cells were cultured in 100 ml of BY-2 culture broth medium at 27° C. until the OD550 value reached 1.1 (about 3 days). 130 µl of 3 mM apigenin (dissolved in 50% aqueous acetonitrile solution containing 0.1% TFA) were added followed by additionally culturing at 27° C. for two and a half days.

Figure 9:
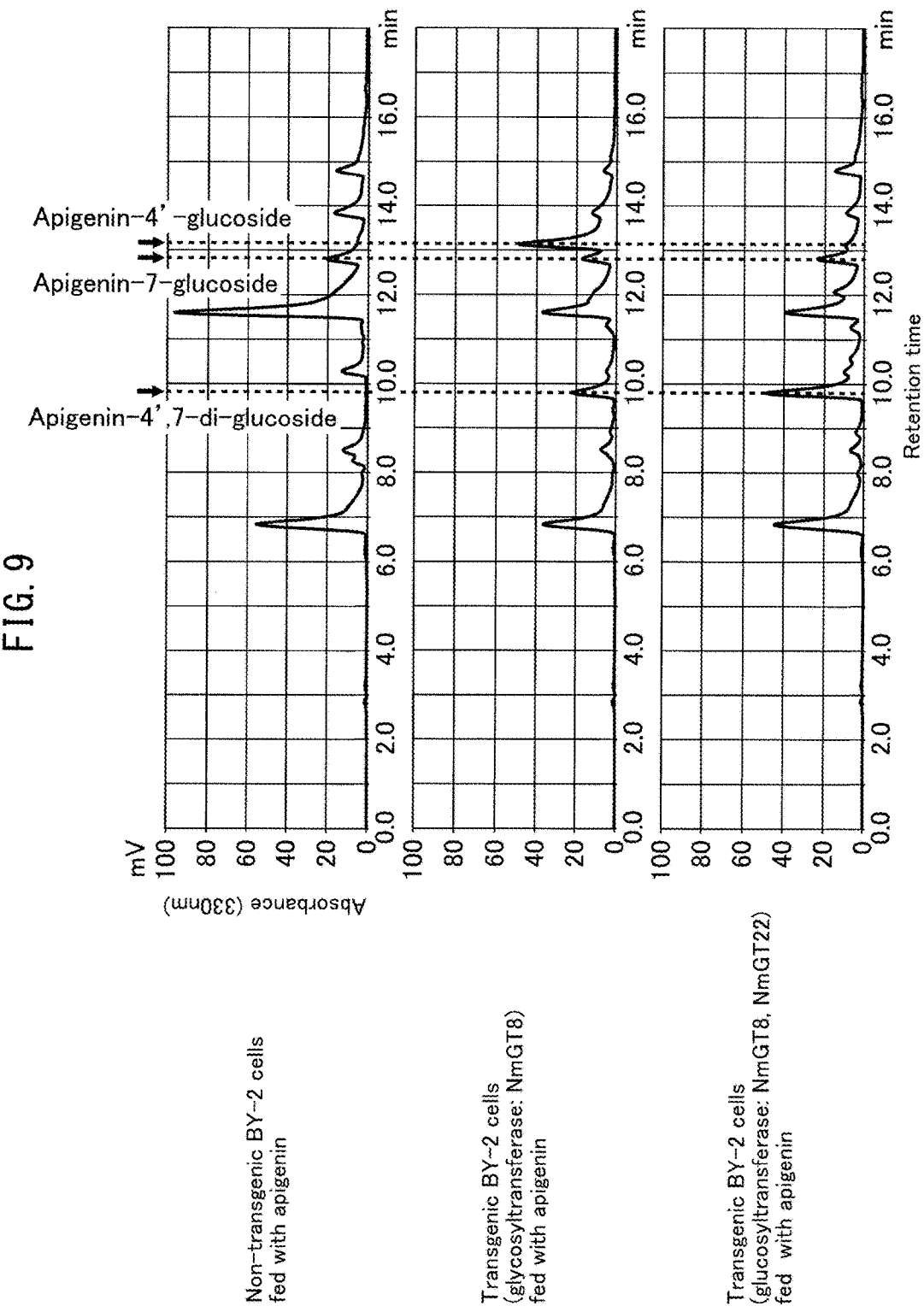
FIG. 9 is a high-performance liquid chromatogram of an extract of transgenic BY2 introduced with NmGT22.

Apigenin-feeding experiments were similarly conducted with BY-2 cells not introduced with a gene and BY-2 cells introduced only with NmGT8 gene for the gene that encodes a protein having activity that transfers a sugar to a hydroxyl group of a flavone to serve as controls. The cell layer obtained by centrifuging the BY-2 culture broth (3,000 rpm, 15° C., 15 minutes) was crushed with a mortar and pestle in liquid nitrogen followed by the addition of 2 ml of extraction buffer (composition: methanol containing 1% HCl) and allowing to stand overnight at normal temperature. The supernatant recovered by centrifuging (3,000 rpm, 15° C., 15 minutes) the cell extract was concentrated to 200 µl using a desiccator. The Himac CF16RX (Hitachi Ltd.) (rotor: T4SS31) was used for centrifugation. The cell extract was additionally centrifuged (15,000 rpm, 15° C., 15 minutes) and the recovered supernatant was passed through a 0.22 µl filter and then analyzed by high-performance liquid chromatography (Prominence, Shimadzu Corp). The MX-205 (Tomy Digital Biology Co., Ltd., rotor: AR015-24) was used for centrifugation. Flavone was detected at 330 nm using the Shimadzu PDA SPD-M10AVP for the detector. The Shim-Pack ODS column (150 mm×4.6 mm, Shimadzu Corp.) was used for the column. A liquid A (0.1% aqueous TFA solution) and a liquid B (90% aqueous methanol solution containing 0.1% TFA) were used for elution. Elution was carried out for 10 minutes at a linear concentration gradient from an 8:2 mixture of the two solutions to a 3:7 mixture of the two solutions followed by eluting for 6 minutes using a 3:7 mixture of the two solutions. The flow rate was 0.6 ml/min. Experiments consisting of feeding apigenin were similarly conducted on BY-2 cells not introduced with a gene and BY-2 cells introduced only with NmGT8 gene for the gene that encodes a protein having activity that transfers a sugar to a hydroxyl group of a flavone to serve as controls followed by analyses of the cell extracts (FIG. 9).

Apigenin 4',7-diglucoside accounted for 0.10% of the biosynthesized flavone compounds present in the cell extract obtained from non-transgenic BY-2 cells, and apigenin 4'-glucoside was not detected. Apigenin 4',7-diglucoside and apigenin 4'-glucoside were determined to account for 10.99% and 31.65%, respectively, of biosynthesized flavone compounds present in the cell extract obtained from transgenic BY-2 cells introduced with NmGT8 only. Apigenin 4',7-diglucoside accounted for 26.35% of the biosynthesized flavone compounds present in the cell extract obtained from transgenic BY-2 cells introduced with NmGT8 and NmGT22, while apigenin 4'-glucoside was not detected. Since the remaining 73.65% constitutes flavone compounds also contained in the cell extract obtained from the control BY-2 cells, these were suggested to be apigenin diglucosides or flavone 7-glucosides and the like biosynthesized by the intrinsic activity of BY-2 cells (FIG. 9).

Apigenin 4'-glucoside, which was detected in the cell extract obtained from BY-2 cells introduced with NmGT8 only, was not detected in the cell extract obtained from transgenic BY-2 cells introduced with NmGT8 and NmGT22. On the basis thereof, NmGT22 was suggested to function as a protein having activity that transfers a sugar to the hydroxyl group at position 7 of apigenin 4'-glucoside by using apigenin 4'-glucoside biosynthesized in BY-2 cells by NmGT8 as substrate. Flavone 4',7-diglucoside can therefore be biosynthesized by co-expression of NmGT22 and NmGT8.

Example 8: Expression of NmGT22 Gene in Rose

<Production of Construct for Expressing NmGT22 Gene in Rose>

The presence or absence of glycosylation of the hydroxyl groups at position 4' and position 7 of a flavone in a rose plant in which NmGT22 and NmGT8 were co-expressed was evaluated in order to confirm that the NmGT22 gene of the present invention encodes a protein having activity that transfers a sugar to the hydroxyl group at position 7 of flavone 4'-glucoside in plants. Torenia flavone synthase was also expressed since roses do not inherently biosynthesize flavones.

A binary vector pSPB6269 was constructed and introduced into a rose plant (variety: Ritapa Humera) in order to co-express NmGT22 and NmGT8 and torenia flavone synthase in the plant. The introduced construct pSPB6269 used the binary vector pBINPLUS (van Engel et al., Transgenic Research 4, p. 288) for the basic skeleton and had an expression cassette consisting of trenia flavone synthase, NmGT22 gene and NmGT8 gene. E1235S promoter (Mitsuhara et al., (1996) Plant Cell Physiol. 37, p. 49) was used for the promoter that expresses each gene.

<Analysis of Expression of NmGT22 in Rose>

Shoots were formed in selective medium containing kanamycin and individuals that were observed to take root were acclimated followed by analyzing gene expression in the same manner as the method described in Example 7 using transgenic rose leaves. As a result, NmGT22 gene was confirmed to have been transcribed in the rose plants.

<Analysis of Function of NmGT22 in BY-2 Cells>

A similar analysis of expression of torenia flavone synthase and NmGT8 was additionally carried out to select a rose strain in which transcription products were synthesized for full-length torenia flavone synthase cDNA, full-length NmGT8 cDNA and full-length NmGT22 cDNA (torenia flavone synthase forward primer: ATGGACACAGTCT-TAATCAC, reverse primer: TCAAGCACCCGATATT-GTG, full-length cDNA: 1539b; NmGT8 forward primer: ATGGAGAAAAAAACTATT, reverse primer: CTATTTC-CAACCATCCAG, full-length cDNA: 1425 b). Flower color pigment was then analyzed for a rose strain in which transcription products were confirmed for the resulting full-length torenia flavone synthase cDNA, full-length NmGT8 cDNA and full-length NmGT22 cDNA. 0.2 g of completely open flower petals were freeze-dried for 24 hours or more followed by finely shredding with a spatula, adding 4 ml of extraction buffer (composition: 50% aqueous acetonitrile solution containing 0.1% TFA), and subjecting to ultrasonic treatment for 20 minutes. The flower petal extract was additionally centrifuged (15,000 rpm, 15° C., 15 minutes) and the recovered supernatant was passed through a 0.22 μm filter followed by analyzing by high-performance liquid chromatography (Prominence, Shimadzu Corp). The MX-205 (Tomy Digital Biology Co., Ltd., rotor: AR015-24) was used for centrifugation. Flavone was detected at 330 nm using the Shimadzu PDA SPD-M10AVP for the high-performance liquid chromatography detector. The Shim-Pack ODS column (150 mm×4.6 mm, Shimadzu Corp.) was used for the column. A liquid A (0.1% aqueous TFA solution) and a liquid B (90% aqueous methanol solution containing 0.1% TFA) were used for elution. Elution was carried out for 90 minutes at a linear concentration gradient from an 8:2 mixture of the two solutions to a 0:10 mixture of the two solutions followed by eluting for 5 minutes using a 0:10 mixture of the two solutions. The flow rate was 0.6 ml/min. Flower petal pigment was similarly analyzed for rose not introduced with a gene and transgenic rose introduced with torenia flavone synthase and NmGT8 only as controls (FIG. 10).

Figure 10:
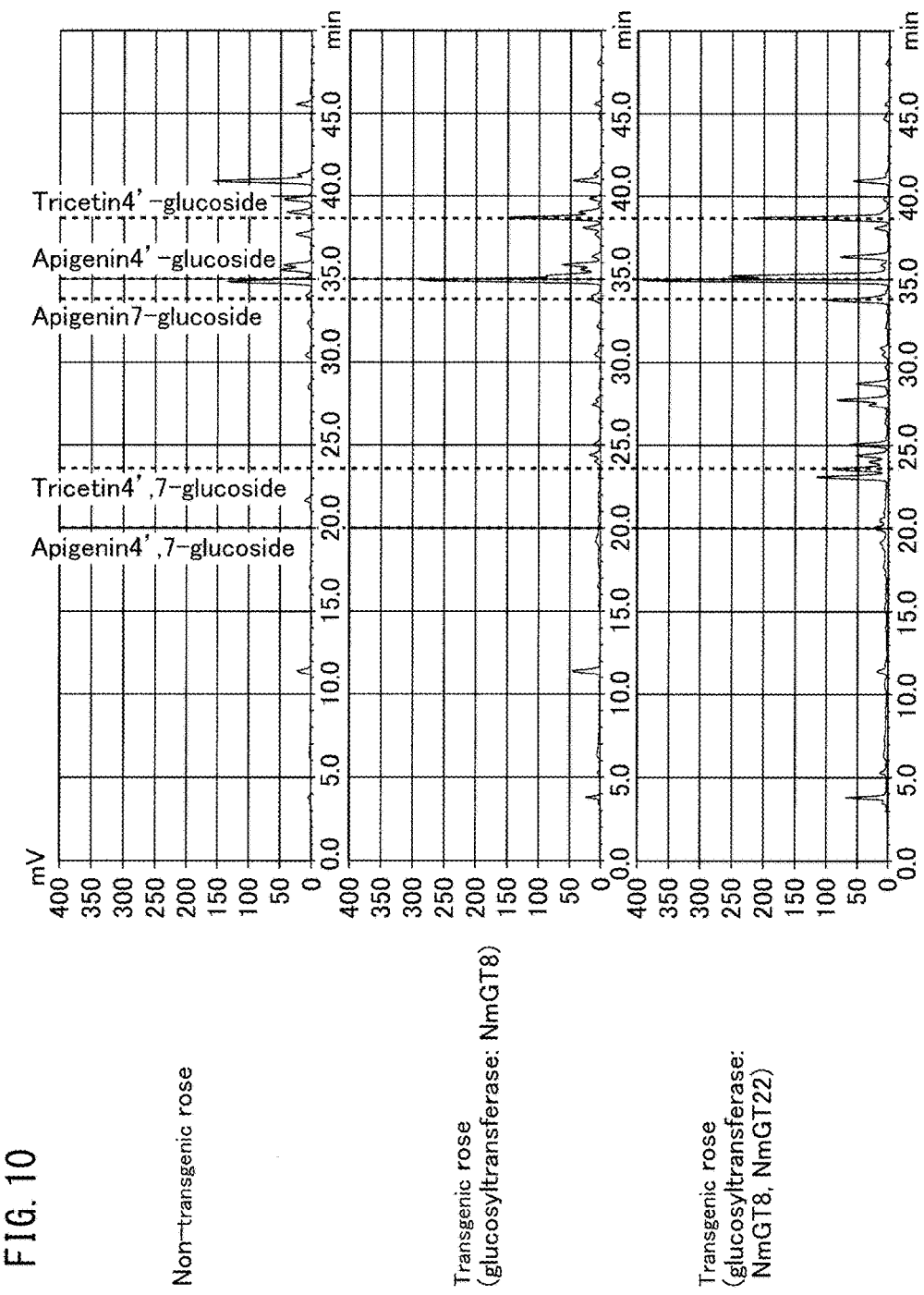
FIG. 10 is a high-performance liquid chromatogram of a flower petal extract of a transgenic rose introduced with NmGT22.

Although flavone 4'-glucoside (apigenin 4'-glucoside, tricetin 4'-glucoside) was detected in transgenic rose introduced with torenia flavone synthase and NmGT8 only, flavone 4',7-diglucoside was not detected (FIG. 10). On the other hand, apigenin 4',7-diglucoside and tricetin 4',7-diglucoside were detected in the transgenic rose introduced with torenia flavone synthase, NmGT8 and NmGT22 (FIG. 10). Flavone 4',7-diglucoside was determined to account for 6.20% of the biosynthesized flavone and flavonol compounds. The remaining 93.80% consists of flavone and flavonol compounds also obtained from the control roses, and they were suggested to be flavone 7-glucoside or flavone 4'-glucoside and the like biosynthesized by rose intrinsic activity and the introduced torenia flavone synthase and NmGT8 (FIG. 10).

Since flavone 4',7-diglucoside, which was not detected from transgenic rose introduced with only torenia flavone synthase and NmGT8, was detected in transgenic rose introduced with torenia flavone synthase, NmGT8 and NmGT22, NmGT22 was suggested to function as a protein having activity that transfers a sugar to the hydroxyl group at position 7 of flavone 4'-glucoside by using flavone 4'-glucoside biosynthesized in rose petals by NmGT8 as substrate. Flavone 4',7-diglucoside can therefore be biosynthesized by co-expression of NmGT22 and NmGT8.

Example 9: Experiment for Acquiring NmGT22-II and Measuring Enzyme Activity

A sequence demonstrating 98% identity with the base sequence of NmGT22 (NmGT22-II (SEQ ID NO: 5)) was acquired in the same manner as Examples 3 and 4.

pET SUMO-NmGT22-II was produced using the method described in Example 4, and enzyme activity was measured using the method described in Example 6. As a result, NmGT22-II was clearly determined to be a protein having activity that transfers a sugar to the hydroxyl group at position 7 of flavone 4'-glucoside in the same manner as NmGT22. In addition, NmGT22-II demonstrated the same tendency as NnGT22 regarding substrate specificity with respect to flavones as well. NmGT22-II is located extremely close to NmGT22 in the phylogenetic tree, and amino acid sequence identity between NmGT22-II and NmGT22 was 99% (FIG. 8, FIG. 11).

The invention claimed is:

1. A recombinant expression vector comprising a polynucleotide selected from the group consisting of the following (a) to (d):
   (a) a polynucleotide comprising the base sequence of SEQ ID NO: 1 or SEQ ID NO: 5;
   (b) a polynucleotide that encodes a protein comprising the amino acid sequence of SEQ ID NO: 2 or SEQ ID NO: 6;
   (c) a polynucleotide that encodes a protein (i) having one to five amino acids deleted, substituted, inserted and/or added in the amino acid sequence of SEQ ID NO: 2 or SEQ ID NO: 6, and (ii) having activity that transfers a sugar to the hydroxyl group at position 7 of a flavone; and,
   (d) a polynucleotide encoding a protein (i) having an amino acid sequence identity of 95% or more with SEQ ID NO: 2 or SEQ ID NO: 6, and (ii) having activity that transfers a sugar to the hydroxyl group at position 7 of a flavone.

2. The recombinant expression vector according to claim 1, wherein the polynucleotide (i) comprises the base sequence of SEQ ID NO: 1 or SEQ ID NO: 5, or (ii) encodes a protein comprising the amino acid sequence of SEQ ID NO: 2 or SEQ ID NO: 6.

3. The recombinant expression vector according to claim 1, wherein the polynucleotide encodes a protein (i) having one to five amino acids deleted, substituted, inserted and/or added in the amino acid sequence of SEQ ID NO: 2 or SEQ ID NO: 6, and (ii) having activity that transfers a sugar to the hydroxyl group at position 7 of flavone 4'-glucoside.

4. The recombinant expression vector according to claim 1, wherein the polynucleotide encodes a protein (i) having an amino acid sequence identity of 95% or more with SEQ ID NO: 2 or SEQ ID NO: 6, and (ii) having activity that transfers a sugar to the hydroxyl group at position 7 of flavone 4'-glucoside.

5. The recombinant expression vector according to claim 1, further comprising a second polynucleotide selected from the group consisting of the following (e) to (h):
   (e) a polynucleotide comprising the base sequence of SEQ ID NO: 3;
   (f) a polynucleotide encoding a protein comprising the amino acid sequence of SEQ ID NO: 4;
   (g) polynucleotide that encodes a protein (i) having one to five amino acids deleted, substituted, inserted and/or added in the amino acid sequence of SEQ ID NO: 4, and (ii) having activity that transfers a sugar to the hydroxyl group at position 4' of a flavone; and,
   (h) a polynucleotide (i) encoding a protein that has activity that transfers a sugar to the hydroxyl group at position 4' of a flavone, and (ii) having a base sequence identity of 95% or more with the base sequence of SEQ ID NO: 3.

6. A non-human host cell comprising the recombinant expression vector according to claim 1.

7. A method for adding a sugar to the hydroxyl group at position 7 of a flavone comprising
   transforming the recombinant expression vector of claim 1 into a non-human host cell;
   producing a protein having activity that transfers the sugar to the hydroxyl group at position 7 of the flavone; and
   allowing the protein to catalyze a reaction to add a sugar to the hydroxyl group at position 7 of the flavone.

8. The method according to claim 7, wherein the flavone is flavone 4'-glucoside.

9. A plant, progeny thereof, portion thereof or tissue thereof introduced with the recombinant expression vector according to claim 1.

10. A plant, progeny thereof, portion thereof or tissue thereof introduced with the recombinant expression vector of claim 5.

11. The portion of a plant according to claim 9, which is a cut flower.

12. A processed cut flower that uses the cut flower according to claim 11.

13. A method for producing a protein having activity that transfers a sugar to the hydroxyl group at position 7 of a flavone, comprising the following steps:
   culturing or growing the non-human host cell according to claim 6, and
   harvesting the protein having activity that transfers the sugar to the hydroxyl group at position 7 of the flavone from the non-human host cell.

14. The method according to claim 13, wherein the flavone is flavone 4'-glucoside.

15. A method for producing a flavone in which a sugar has been added to the hydroxyl group at position 7, comprising the following steps:
   culturing or growing the non-human host cell according to claim 6, and
   harvesting the flavone in which the sugar has been added to the hydroxyl group at position 7 from the non-human host cell.

16. The method according to claim 15, wherein a sugar is also added to the hydroxyl group at position 4' of the flavone.

17. The recombinant expression vector according to claim 1, wherein the polynucleotide is operably linked to a promoter.

18. The recombinant expression vector of claim 17, wherein the promoter is selected from the group consisting of a bacterial promoter, a yeast promoter, a mold promoter, a and a promoter for use with animal cell hosts.

19. The recombinant expression vector of claim 17, wherein the promoter constitutively expresses a gene in plant cells.

20. The recombinant expression vector of claim 19, wherein the promoter is selected from the group consisting of cauliflower mosaic virus 35 S RNA promoter, rd29A gene promoter, rbcS promoter, and mac-1 promoter.

21. The recombinant expression vector of claim 17, wherein the promoter specifically expresses a gene in a plant tissue.

22. The non-human host cell according to claim 6, being a prokaryotic organism cell or an eukaryotic microorganism cell.

* * * * *

SEQUENCE LISTING

<160> NUMBER OF SEQ ID NOS: 13

<210> SEQ ID NO 1
<211> LENGTH: 1431
<212> TYPE: DNA
<213> ORGANISM: Nemophila menziesii

<400> SEQUENCE: 1

```
atggaatgca aaaatccaga ttctcttcat gtttttctcg tttccgcccc gggccaaggg      60
aacgttacgc caatgcttag actagcaaaa tccctcgctt caaagggtct actcgtcaca     120
ttctccactc ccgaaagtta tggcaaagaa atgcggaaaa ctaacgatga tatctccgat     180
caaccaatcc tcatcggcga aggaagtatc aggtttgaat ttctcgacga tgaatgggac     240
gagaatgaac ataaaggtga agggctcgat gcatacgcta ctcatttgga gcgcgttggc     300
aaacaaaacc tccctcgaat gtttaaaaag catgaggaag aaggtcgtcc catttcgtgc     360
ataatcaaca atcctttcat tccgtgggtc ccagaggtta ccgaaagcct tggtatccct     420
agtgctctcc tatgggtaca atcttgtgct agcttttcga gttattatca tttcttcaac     480
gatcttgttt ctttcccgac cgagtctaat cttaaaaaag acgtttgctt gccatctatg     540
cctatgttga aatacgatga ggtgccgttg cttttatacc ctatcgttcc tttaccgatc     600
atatcactca agaacgcaat gcttcgtcaa caaaagaatt tgtcaaaaac attttgtgtg     660
ttagtggaca cgtttcaaca actagaagac gagctaattc actacctttc caagctttgc     720
cccataagac caatcggccc tttattcaaa atctctgaca cttcaagctc gaacattagt     780
ggtgacatca gaaaggcgga tgattgcatc gagtggctag actcaaagtc accctcctcg     840
gtcgtgtaca tatccttcgg aagcattgtt catttaaaac aagaacaaat tactgagata     900
gcgtatgcac tcatgaatat aaacatatcg ttcttgtggg tcatgaagcc gcctcaaaag     960
gattcttatg ataaacaaca tgttttacca caagggttct tggaaaaagt tggtgagaaa    1020
ggtaaagttg tgaaatggag tcctcaagaa caagtgttgt cacaccaatc tttggcttgt    1080
tttgtaacac attgtggttg gaattcatct atggaggctc ttgctaatgg tatacgagtg    1140
gttactttac ctcaatgggg tgatcaagtc actaatgcta agttcttggt ggatgttttt    1200
ggagttggtg ttagactatc tagaggcgac ttagaagata gaatcatccc gagagaagag    1260
atagagttga gattgctaga ggttactagc ggcgaaaagg ctacagaaat gaagcataat    1320
gcattgaggt ggaagaaggc ggctgaggag gcggtggcta aggatggctc ctctagcaaa    1380
aatctgcaag agtttgtaga cgagctcaat aatttcagat ttattaccta g             1431
```

<210> SEQ ID NO 2
<211> LENGTH: 476
<212> TYPE: PRT
<213> ORGANISM: Nemophila menziesii

<400> SEQUENCE: 2

```
Met Glu Cys Lys Asn Pro Asp Ser Leu His Val Phe Leu Val Ser Ala
1               5                   10                  15

Pro Gly Gln Gly Asn Val Thr Pro Met Leu Arg Leu Ala Lys Ser Leu
            20                  25                  30

Ala Ser Lys Gly Leu Leu Val Thr Phe Ser Thr Pro Glu Ser Tyr Gly
```

```
                35                  40                  45
Lys Glu Met Arg Lys Thr Asn Asp Asp Ile Ser Asp Gln Pro Ile Leu
 50                  55                  60

Ile Gly Glu Gly Ser Ile Arg Phe Glu Phe Leu Asp Asp Glu Trp Asp
 65                  70                  75                  80

Glu Asn Glu His Lys Gly Glu Gly Leu Asp Ala Tyr Ala Thr His Leu
                 85                  90                  95

Glu Arg Val Gly Lys Gln Asn Leu Pro Arg Met Phe Lys Lys His Glu
                100                 105                 110

Glu Glu Gly Arg Pro Ile Ser Cys Ile Ile Asn Asn Pro Phe Ile Pro
                115                 120                 125

Trp Val Pro Glu Val Ala Glu Ser Leu Gly Ile Pro Ser Ala Leu Leu
130                 135                 140

Trp Val Gln Ser Cys Ala Ser Phe Ser Ser Tyr Tyr His Phe Phe Asn
145                 150                 155                 160

Asp Leu Val Ser Phe Pro Thr Glu Ser Asn Leu Lys Lys Asp Val Cys
                165                 170                 175

Leu Pro Ser Met Pro Met Leu Lys Tyr Asp Glu Val Pro Leu Leu Leu
                180                 185                 190

Tyr Pro Ile Val Pro Leu Pro Ile Ile Ser Leu Lys Asn Ala Met Leu
                195                 200                 205

Arg Gln Gln Lys Asn Leu Ser Lys Thr Phe Cys Val Leu Val Asp Thr
210                 215                 220

Phe Gln Gln Leu Glu Asp Glu Leu Ile His Tyr Leu Ser Lys Leu Cys
225                 230                 235                 240

Pro Ile Arg Pro Ile Gly Pro Leu Phe Lys Ile Ser Asp Thr Ser Ser
                245                 250                 255

Ser Asn Ile Ser Gly Asp Ile Arg Lys Ala Asp Asp Cys Ile Glu Trp
                260                 265                 270

Leu Asp Ser Lys Ser Pro Ser Ser Val Val Tyr Ile Ser Phe Gly Ser
                275                 280                 285

Ile Val His Leu Lys Gln Glu Gln Ile Thr Glu Ile Ala Tyr Ala Leu
                290                 295                 300

Met Asn Ile Asn Ile Ser Phe Leu Trp Val Met Lys Pro Pro Gln Lys
305                 310                 315                 320

Asp Ser Tyr Asp Lys Gln His Val Leu Pro Gln Gly Phe Leu Glu Lys
                325                 330                 335

Val Gly Glu Lys Gly Lys Val Val Lys Trp Ser Pro Gln Glu Gln Val
                340                 345                 350

Leu Ser His Gln Ser Leu Ala Cys Phe Val Thr His Cys Gly Trp Asn
                355                 360                 365

Ser Ser Met Glu Ala Leu Ala Asn Gly Ile Arg Val Val Thr Leu Pro
370                 375                 380

Gln Trp Gly Asp Gln Val Thr Asn Ala Lys Phe Leu Val Asp Val Phe
385                 390                 395                 400

Gly Val Gly Val Arg Leu Ser Arg Gly Asp Leu Glu Asp Arg Ile Ile
                405                 410                 415

Pro Arg Glu Glu Ile Glu Leu Arg Leu Leu Val Thr Ser Gly Glu
                420                 425                 430

Lys Ala Thr Glu Met Lys His Asn Ala Leu Arg Trp Lys Lys Ala Ala
                435                 440                 445

Glu Glu Ala Val Ala Lys Asp Gly Ser Ser Ser Lys Asn Leu Gln Glu
                450                 455                 460
```

Phe Val Asp Glu Leu Asn Asn Phe Arg Phe Ile Thr
465                 470                 475

<210> SEQ ID NO 3
<211> LENGTH: 1425
<212> TYPE: DNA
<213> ORGANISM: Nemophila menziesii

<400> SEQUENCE: 3

| | | |
|---|---|---|
| atggagaaaa aaactattat tctgtatccc tctccaggca taggtcactt agtttccatg | 60 |
| gttgagcttg ctaagctcat tcttaatcgt gaaccatcat actccatcat tatctttatt | 120 |
| tcttcagcac catactctac tggctcaagt gcccttata ttagccatgt ttcagccacc | 180 |
| acatcaggca tctccttcca ccacctccct gtcctcgtcc ttcccccaa caccttcagc | 240 |
| tccttcgaag aaatagcata taaaattcct caacttaaca atcccaattt aaaactagcc | 300 |
| cttcaaacaa tctccaaaga tcaagtgat ctcaaagcct tcatcataga cttcttctgc | 360 |
| actgctgcag ttgaagtctc ttcaaacctt gaaattccta cctatttctt ctttacatct | 420 |
| ggttcttctg ctatgtgtca attcctatac cttccaactc ttcatgaaac cataacccaa | 480 |
| aaagacttgc aagatcctaa cacttacgtt cacattccag gtattccacc tatccattct | 540 |
| ttagacttgc ctaaggtttt atccaatagg agtaccgtgt tatataaaga gcttataaac | 600 |
| actgcaaacc agatggcaaa gtgttctgga atcttgataa acgcatttga acacttgaa | 660 |
| ccaaaagctg tcaaagcatt aaagaaggt ttatgcaccc ctggtatgcc aactccacct | 720 |
| gtttattgta tcggaccgct tatcgctagc ggtgataaag gaaatggcaa taatgctcat | 780 |
| gggcatgaga ttttaacttg gttaaactct caacctagta aaagtgttgt gtttctatgc | 840 |
| tttggtagtt taggtacttt taaggaagat cagttgaagg aaattgctat agggttggaa | 900 |
| aatagtggcc ataggttttt atgggtaatg aaaagtccac ctattgatga caaaaccaag | 960 |
| cgtttcttac caccaccaga gccagatttt aatgtattat tgcctgaagg ttttttggag | 1020 |
| agaactaaag aaagaggagt tattgtgaag tcatgggcgc tcaattggc tatattgaat | 1080 |
| catgatgcaa taggcggatt tgttactcat tgcggttgga actcagtttt ggaagctatt | 1140 |
| tgtggtggtg tgccaatgtt agcatggcca ttatatgctg agcaaagggt gaatagagta | 1200 |
| tgtatggtgg aagagatgaa ggtggcgctg ccattggagg agtctgtaga tgggtttgta | 1260 |
| atggcatcgg agattgagaa agagttaag gaattggtgg attatgagag tagtgaagca | 1320 |
| attagagatc aagttaagat aatgagtgaa aaagctaaaa ctgcagttgc agttagtgga | 1380 |
| tcatcccatg atgcattgac caaactactg gatggttgga aatag | 1425 |

<210> SEQ ID NO 4
<211> LENGTH: 474
<212> TYPE: PRT
<213> ORGANISM: Nemophila menziesii

<400> SEQUENCE: 4

Met Glu Lys Lys Thr Ile Ile Leu Tyr Pro Ser Pro Gly Ile Gly His
1               5                   10                  15

Leu Val Ser Met Val Glu Leu Ala Lys Leu Ile Leu Asn Arg Glu Pro
            20                  25                  30

Ser Tyr Ser Ile Ile Ile Phe Ile Ser Ser Ala Pro Tyr Ser Thr Gly
        35                  40                  45

Ser Ser Ala Pro Tyr Ile Ser His Val Ser Ala Thr Thr Ser Gly Ile
    50                  55                  60

```
Ser Phe His His Leu Pro Val Leu Val Leu Pro Pro Asn Thr Phe Ser
 65                  70                  75                  80

Ser Phe Glu Glu Ile Ala Tyr Lys Ile Pro Gln Leu Asn Asn Pro Asn
                 85                  90                  95

Leu Lys Leu Ala Leu Gln Thr Ile Ser Lys Glu Ser Ser Asp Leu Lys
            100                 105                 110

Ala Phe Ile Ile Asp Phe Phe Cys Thr Ala Ala Val Glu Val Ser Ser
        115                 120                 125

Asn Leu Glu Ile Pro Thr Tyr Phe Phe Thr Ser Gly Ser Ser Ala
    130                 135                 140

Met Cys Gln Phe Leu Tyr Leu Pro Thr Leu His Glu Thr Ile Thr Gln
145                 150                 155                 160

Lys Asp Leu Gln Asp Pro Asn Thr Tyr Val His Ile Pro Gly Ile Pro
                165                 170                 175

Pro Ile His Ser Leu Asp Leu Pro Lys Val Leu Ser Asn Arg Ser Thr
            180                 185                 190

Val Leu Tyr Lys Glu Leu Ile Asn Thr Ala Asn Gln Met Ala Lys Cys
        195                 200                 205

Ser Gly Ile Leu Ile Asn Ala Phe Glu Thr Leu Glu Pro Lys Ala Val
    210                 215                 220

Lys Ala Leu Lys Glu Gly Leu Cys Thr Pro Gly Met Pro Thr Pro Pro
225                 230                 235                 240

Val Tyr Cys Ile Gly Pro Leu Ile Ala Ser Gly Asp Lys Gly Asn Gly
                245                 250                 255

Asn Asn Ala His Gly His Glu Ile Leu Thr Trp Leu Asn Ser Gln Pro
            260                 265                 270

Ser Lys Ser Val Val Phe Leu Cys Phe Gly Ser Leu Gly Thr Phe Lys
        275                 280                 285

Glu Asp Gln Leu Lys Glu Ile Ala Ile Gly Leu Glu Asn Ser Gly His
    290                 295                 300

Arg Phe Leu Trp Val Met Lys Ser Pro Pro Ile Asp Asp Lys Thr Lys
305                 310                 315                 320

Arg Phe Leu Pro Pro Glu Pro Asp Phe Asn Val Leu Leu Pro Glu
                325                 330                 335

Gly Phe Leu Glu Arg Thr Lys Glu Arg Gly Val Ile Val Lys Ser Trp
            340                 345                 350

Ala Pro Gln Leu Ala Ile Leu Asn His Asp Ala Ile Gly Gly Phe Val
        355                 360                 365

Thr His Cys Gly Trp Asn Ser Val Leu Glu Ala Ile Cys Gly Gly Val
    370                 375                 380

Pro Met Leu Ala Trp Pro Leu Tyr Ala Glu Gln Arg Val Asn Arg Val
385                 390                 395                 400

Cys Met Val Glu Glu Met Lys Val Ala Leu Pro Leu Glu Glu Ser Val
                405                 410                 415

Asp Gly Phe Val Met Ala Ser Glu Ile Glu Lys Arg Val Lys Glu Leu
            420                 425                 430

Val Asp Tyr Glu Ser Ser Glu Ala Ile Arg Asp Gln Val Lys Ile Met
        435                 440                 445

Ser Glu Lys Ala Lys Thr Ala Val Ala Val Ser Gly Ser Ser His Asp
    450                 455                 460

Ala Leu Thr Lys Leu Leu Asp Gly Trp Lys
465                 470
```

<210> SEQ ID NO 5
<211> LENGTH: 1431
<212> TYPE: DNA
<213> ORGANISM: Nemophila menziesii

<400> SEQUENCE: 5

| | | | | |
|---|---|---|---|---|
| atggaatgca | aaaatccaga | ttctcttcat | gtttttctcg | tttccgcccc gggccaaggg | 60 |
| aacgttacgc | caatgcttag | actagcaaaa | tccctcgctt | caaagggtct actcgtcaca | 120 |
| ttctccactc | cagaaagtta | tggcaaagaa | atgcggaaaa | ctaacaatga tatctccgat | 180 |
| caaccaatcc | tcatcggcga | aggaatcatc | aggtttgaat | tcttgacga tgaatgggac | 240 |
| gagaatgaac | ataaaggtga | agggctcgat | gcatacgcta | ctcatttgga gcgcgttggc | 300 |
| aaacaaatac | tccctcgaat | gtttaaaaag | catgaggaag | aaggtcgtcc catttcgtgc | 360 |
| ataatcaaca | atcctttcat | tccgtgggtc | ccagaggttg | ctgaaagcct tggtattcct | 420 |
| agtgctctcc | tatgggtaca | atcttgtgct | agcttttcta | gttattatca tttcttcaac | 480 |
| gatcttgttt | ctttccctac | cgagtctaat | cttaaaaaag | acgttgcttt gccatctatg | 540 |
| cctatgttga | aatacgatga | ggtgccttg | ctattatacc | ctatcgttcc tttaccgatc | 600 |
| atatcactca | agaacgcaat | gcttcgtcaa | caaaagaatt | tgtcaaaaac attttgcgtg | 660 |
| ttagtggaca | cgtttcaaca | actagaaagac | gagctaattc | actacctttc caagctttgc | 720 |
| cccataagac | caatcggccc | tttattcaaa | atctctgaca | cttcaagctc gaacattagt | 780 |
| ggtgacatca | gaaaggcgga | tgattgcatc | gagtggctag | actcaaagtc accctcctcg | 840 |
| gtcgtgtaca | tatccttcgg | aagcattgtt | catttaaaac | aagaacaaat tactgagata | 900 |
| gcgtatgcac | tcatgaatat | aaacatatcg | ttcttgtggg | tcatgaagcc gcctcaaaag | 960 |
| gattcttatg | ataaacaaca | tgttttacca | aagggttct | tggaaaaagt tggtgagaaa | 1020 |
| ggtaaagttg | tgaaatggag | tcctcaagaa | caagtgttgt | cacaccaatc tttggcttgt | 1080 |
| tttgtaacac | attgtggttg | gaattcatct | atggaggctc | ttgctaatgg tatacgagtg | 1140 |
| gtaactttac | ctcaatgggg | tgatcaagtc | actaatgcta | agttcttggt ggatgttttt | 1200 |
| ggagttggtg | ttagactatc | tagaggcgac | ttagaagata | gaatcatccc gagagaagag | 1260 |
| atagagttga | gattgctaga | ggttactagc | ggcgaaaagg | ctacagaaat gaagcataat | 1320 |
| gcattgaggt | ggaagaaggc | ggctgaggag | gcggtggcta | aggatggctc ctctagcaaa | 1380 |
| aatctgcaag | agtttgtaga | cgagctcaat | aatttcagat | ttattaccta g | 1431 |

<210> SEQ ID NO 6
<211> LENGTH: 476
<212> TYPE: PRT
<213> ORGANISM: Nemophila menziesii

<400> SEQUENCE: 6

Met Glu Cys Lys Asn Pro Asp Ser Leu His Val Phe Leu Val Ser Ala
1               5                   10                  15

Pro Gly Gln Gly Asn Val Thr Pro Met Leu Arg Leu Ala Lys Ser Leu
            20                  25                  30

Ala Ser Lys Gly Leu Leu Val Thr Phe Ser Thr Pro Glu Ser Tyr Gly
        35                  40                  45

Lys Glu Met Arg Lys Thr Asn Asn Asp Ile Ser Asp Gln Pro Ile Leu
    50                  55                  60

Ile Gly Glu Gly Ile Ile Arg Phe Glu Phe Leu Asp Asp Glu Trp Asp
65                  70                  75                  80

```
Glu Asn Glu His Lys Gly Glu Gly Leu Asp Ala Tyr Ala Thr His Leu
                 85                  90                  95

Glu Arg Val Gly Lys Gln Ile Leu Pro Arg Met Phe Lys Lys His Glu
            100                 105                 110

Glu Glu Gly Arg Pro Ile Ser Cys Ile Ile Asn Asn Pro Phe Ile Pro
        115                 120                 125

Trp Val Pro Glu Val Ala Glu Ser Leu Gly Ile Pro Ser Ala Leu Leu
130                 135                 140

Trp Val Gln Ser Cys Ala Ser Phe Ser Ser Tyr Tyr His Phe Phe Asn
145                 150                 155                 160

Asp Leu Val Ser Phe Pro Thr Glu Ser Asn Leu Lys Lys Asp Val Cys
                165                 170                 175

Leu Pro Ser Met Pro Met Leu Lys Tyr Asp Glu Val Pro Leu Leu Leu
            180                 185                 190

Tyr Pro Ile Val Pro Leu Pro Ile Ile Ser Leu Lys Asn Ala Met Leu
        195                 200                 205

Arg Gln Gln Lys Asn Leu Ser Lys Thr Phe Cys Val Leu Val Asp Thr
210                 215                 220

Phe Gln Gln Leu Glu Asp Glu Leu Ile His Tyr Leu Ser Lys Leu Cys
225                 230                 235                 240

Pro Ile Arg Pro Ile Gly Pro Leu Phe Lys Ile Ser Asp Thr Ser Ser
                245                 250                 255

Ser Asn Ile Ser Gly Asp Ile Arg Lys Ala Asp Asp Cys Ile Glu Trp
            260                 265                 270

Leu Asp Ser Lys Ser Pro Ser Ser Val Val Tyr Ile Ser Phe Gly Ser
        275                 280                 285

Ile Val His Leu Lys Gln Glu Gln Ile Thr Glu Ile Ala Tyr Ala Leu
290                 295                 300

Met Asn Ile Asn Ile Ser Phe Leu Trp Val Met Lys Pro Pro Gln Lys
305                 310                 315                 320

Asp Ser Tyr Asp Lys Gln His Val Leu Pro Gln Gly Phe Leu Glu Lys
                325                 330                 335

Val Gly Glu Lys Gly Lys Val Val Lys Trp Ser Pro Gln Glu Gln Val
            340                 345                 350

Leu Ser His Gln Ser Leu Ala Cys Phe Val Thr His Cys Gly Trp Asn
        355                 360                 365

Ser Ser Met Glu Ala Leu Ala Asn Gly Ile Arg Val Val Thr Leu Pro
370                 375                 380

Gln Trp Gly Asp Gln Val Thr Asn Ala Lys Phe Leu Val Asp Val Phe
385                 390                 395                 400

Gly Val Gly Val Arg Leu Ser Arg Gly Asp Leu Glu Asp Arg Ile Ile
                405                 410                 415

Pro Arg Glu Glu Ile Glu Leu Arg Leu Leu Glu Val Thr Ser Gly Glu
            420                 425                 430

Lys Ala Thr Glu Met Lys His Asn Ala Leu Arg Trp Lys Lys Ala Ala
        435                 440                 445

Glu Glu Ala Val Ala Lys Asp Gly Ser Ser Ser Lys Asn Leu Gln Glu
450                 455                 460

Phe Val Asp Glu Leu Asn Asn Phe Arg Phe Ile Thr
465                 470                 475

<210> SEQ ID NO 7
<211> LENGTH: 23
<212> TYPE: DNA
```

```
<213> ORGANISM: Artificial Sequence
<220> FEATURE:
<223> OTHER INFORMATION: Forward primer

<400> SEQUENCE: 7
atggaatgca aaatccaga ttc                                              23

<210> SEQ ID NO 8
<211> LENGTH: 25
<212> TYPE: DNA
<213> ORGANISM: Artificial Sequence
<220> FEATURE:
<223> OTHER INFORMATION: Reverse primer

<400> SEQUENCE: 8
ctaggtaata aatctgaaat tattg                                           25

<210> SEQ ID NO 9
<211> LENGTH: 18
<212> TYPE: DNA
<213> ORGANISM: Artificial Sequence
<220> FEATURE:
<223> OTHER INFORMATION: Forward primer

<400> SEQUENCE: 9
atggagaaaa aaactatt                                                   18

<210> SEQ ID NO 10
<211> LENGTH: 18
<212> TYPE: DNA
<213> ORGANISM: Artificial Sequence
<220> FEATURE:
<223> OTHER INFORMATION: Reverse primer

<400> SEQUENCE: 10
ctatttccaa ccatccag                                                   18

<210> SEQ ID NO 11
<211> LENGTH: 20
<212> TYPE: DNA
<213> ORGANISM: Artificial Sequence
<220> FEATURE:
<223> OTHER INFORMATION: Forward primer

<400> SEQUENCE: 11
atggacacag tcttaatcac                                                 20

<210> SEQ ID NO 12
<211> LENGTH: 19
<212> TYPE: DNA
<213> ORGANISM: Artificial Sequence
<220> FEATURE:
<223> OTHER INFORMATION: Reverse primer

<400> SEQUENCE: 12
tcaagcaccc gatattgtg                                                  19

<210> SEQ ID NO 13
<211> LENGTH: 479
<212> TYPE: PRT
<213> ORGANISM: Vitis vinifera
<220> FEATURE:
<221> NAME/KEY: MISC_FEATURE
<222> LOCATION: (1)..(479)
<223> OTHER INFORMATION: glucosyltransferase encoded by GenBank
      Accession No. JN164680
```

<400> SEQUENCE: 13

```
Met Gly Ser Glu Ser Lys Leu Val His Val Phe Leu Val Ser Phe Pro
 1               5                  10                  15
Gly Gln Gly His Val Asn Pro Leu Leu Arg Leu Gly Lys Arg Leu Ala
             20                  25                  30
Ser Lys Gly Leu Leu Val Thr Phe Thr Thr Pro Glu Ser Ile Gly Lys
         35                  40                  45
Gln Met Arg Lys Ala Ser Asn Ile Thr Asp Gln Pro Thr Pro Val Gly
     50                  55                  60
Asp Gly Met Ile Arg Phe Glu Phe Phe Glu Asp Gly Trp Asp Glu Asn
 65                  70                  75                  80
Glu Pro Lys Arg Gln Asp Leu Asp Leu Tyr Leu Pro Gln Leu Glu Leu
                 85                  90                  95
Val Gly Lys Lys Ile Ile Pro Glu Met Ile Lys Lys Asn Ala Glu Gln
            100                 105                 110
Asp Arg Pro Val Ser Cys Leu Ile Asn Asn Pro Phe Ile Pro Trp Val
        115                 120                 125
Ser Asp Val Ala Ala Asp Leu Gly Leu Pro Ser Ala Met Leu Trp Val
130                 135                 140
Gln Ser Cys Ala Cys Leu Ser Thr Tyr Tyr His Tyr His Gly Leu
145                 150                 155                 160
Val Pro Phe Pro Ser Glu Ala Glu Pro Glu Ile Asp Val Gln Leu Pro
                165                 170                 175
Cys Met Pro Leu Leu Lys Tyr Asp Glu Ile Ala Ser Phe Leu Tyr Pro
            180                 185                 190
Thr Thr Pro Tyr Pro Phe Leu Arg Arg Ala Ile Leu Gly Gln Tyr Lys
        195                 200                 205
Asn Leu Asp Lys Pro Phe Cys Ile Leu Met Asp Thr Phe Gln Glu Leu
    210                 215                 220
Glu Pro Glu Val Ile Glu Tyr Met Ser Lys Ile Cys Pro Ile Lys Pro
225                 230                 235                 240
Val Gly Pro Leu Tyr Lys Asn Pro Lys Val Pro Asn Ala Ala Val Arg
                245                 250                 255
Gly Asp Phe Met Lys Ala Asp Asp Cys Ile Glu Trp Leu Asp Ser Lys
            260                 265                 270
Pro Pro Ser Ser Val Val Tyr Ile Ser Phe Gly Ser Val Val Tyr Leu
        275                 280                 285
Lys Gln Glu Gln Val Asp Glu Ile Ala Tyr Gly Leu Leu Asn Ser Gly
    290                 295                 300
Val Gln Phe Leu Trp Val Met Lys Pro Pro His Lys Asp Ala Gly Leu
305                 310                 315                 320
Glu Leu Leu Val Leu Pro Glu Gly Phe Leu Glu Lys Ala Gly Asp Lys
                325                 330                 335
Gly Lys Val Val Gln Trp Ser Pro Gln Glu Gln Val Leu Ala His Pro
            340                 345                 350
Ser Val Ala Cys Phe Val Thr His Cys Gly Trp Asn Ser Ser Met Glu
        355                 360                 365
Ala Leu Ser Ser Gly Met Pro Val Val Ala Phe Pro Gln Trp Gly Asp
    370                 375                 380
Gln Val Thr Asp Ala Lys Tyr Leu Val Asp Val Phe Lys Val Gly Val
385                 390                 395                 400
Arg Met Cys Arg Gly Glu Ala Glu Asn Lys Leu Ile Thr Arg Asp Glu
                405                 410                 415
```

-continued

```
Val Glu Lys Cys Leu Ile Glu Ala Thr Thr Gly Glu Lys Ala Ala Glu
            420                 425                 430

Leu Lys Glu Asn Thr Met Lys Trp Lys Lys Ala Ala Glu Glu Ala Val
        435                 440                 445

Ala Glu Gly Gly Ser Ser Asp Arg Asn Leu Gln Glu Phe Val Asp Glu
    450                 455                 460

Val Arg Arg Met Ser Met Glu Leu Val Cys Lys Ser Lys Lys Ile
465                 470                 475
```